United States Patent
Urisu et al.

(10) Patent No.: US 9,829,477 B2
(45) Date of Patent: Nov. 28, 2017

(54) FORMATION AND USE OF NEURONAL NETWORK, AND NEURON SEEDING DEVICE

(71) Applicant: JAPAN SCIENCE AND TECHNOLOGY AGENCY, Saitama (JP)

(72) Inventors: Tsuneo Urisu, Aichi (JP); Zhi-hong Wang, Aichi (JP); Hidetaka Uno, Aichi (JP); Miho Saitoh, Aichi (JP); Yasutaka Nagaoka, Aichi (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 14/429,035

(22) PCT Filed: Mar. 21, 2013

(86) PCT No.: PCT/JP2013/057976
§ 371 (c)(1),
(2) Date: Mar. 18, 2015

(87) PCT Pub. No.: WO2014/045618
PCT Pub. Date: Mar. 27, 2014

(65) Prior Publication Data
US 2015/0233890 A1    Aug. 20, 2015

(30) Foreign Application Priority Data
Sep. 19, 2012   (JP) .................................. 2012-205561

(51) Int. Cl.
C12M 1/32       (2006.01)
G01N 33/487     (2006.01)
(Continued)

(52) U.S. Cl.
CPC ....... *G01N 33/48728* (2013.01); *C12M 23/12* (2013.01); *C12M 23/38* (2013.01); *C12M 33/04* (2013.01)

(58) Field of Classification Search
CPC . G01N 33/48728; C12M 23/12; C12M 23/38; C12M 33/04
(Continued)

(56) References Cited

U.S. PATENT DOCUMENTS

2002/0182627 A1* 12/2002 Wang ................ B01L 3/502761
                                                      435/6.11
2003/0036196 A1    2/2003 Okano et al.
(Continued)

FOREIGN PATENT DOCUMENTS

CN   101629143       1/2010
JP   H07-075547 A    3/1995
(Continued)

OTHER PUBLICATIONS

International Search Report received for PCT Patent Application No. PCT/JP2013/057976 dated May 21, 2013, 3 pages.
(Continued)

*Primary Examiner* — Michael Hobbs
(74) *Attorney, Agent, or Firm* — Amster, Rothstein & Ebenstein LLP

(57) ABSTRACT

A planar patch clamp device is disclosed, which can be used for culturing a neuron in the device so as to form a neuron network, and detecting an electrical property of the neuron that forms the neuron network. The planar patch clamp device includes a plurality of protrusions formed on a first surface, an extracellular matrix forming substance which is coated on the peripheries of a through hole, and electrode sections.

6 Claims, 12 Drawing Sheets

(51) Int. Cl.
*C12M 1/00* (2006.01)
*C12M 1/26* (2006.01)

(58) Field of Classification Search
USPC ........................................... 435/287.9
See application file for complete search history.

(56) References Cited

U.S. PATENT DOCUMENTS

| | | | |
|---|---|---|---|
| 2003/0070923 A1* | 4/2003 | Schroeder | G01N 33/48728 204/400 |
| 2004/0209352 A1 | 10/2004 | Ozaki et al. | |
| 2005/0279634 A1 | 12/2005 | Ozaki et al. | |
| 2006/0183222 A1* | 8/2006 | Kuwabara | C12M 25/00 435/368 |
| 2010/0221301 A1 | 9/2010 | Le Visage et al. | |

FOREIGN PATENT DOCUMENTS

| | | |
|---|---|---|
| JP | 2004-166692 A | 6/2004 |
| JP | 2009-156572 A | 7/2009 |
| JP | 2009-204407 A | 9/2009 |
| JP | 4567936 B2 | 8/2010 |
| JP | 2010-227012 A | 10/2010 |
| JP | 2010-227087 A | 10/2010 |
| JP | 2011-500119 A | 1/2011 |
| JP | 2011-193758 A | 10/2011 |
| WO | 2005/001018 A1 | 1/2005 |
| WO | 2005/116242 A1 | 12/2005 |
| WO | 2007/116978 A1 | 10/2007 |

OTHER PUBLICATIONS

Zeck G et al., "Noninvasive neuroelectronic interfacing with synaptically connected snail neurons immobilized on a semiconductor chip", PNAS, vol. 98, No. 18, pp. 10457-10462 (Aug. 28, 2001).

* cited by examiner

FORMATION AND USE OF NEURONAL NETWORK, AND NEURON SEEDING DEVICE

CROSS-REFERENCE TO RELATED APPLICATIONS

This application is a U.S. national stage entry under 35 U.S.C. §371 of PCT International Patent Application No. PCT/JP2013/057976, filed Mar. 21, 2013, which claims the benefit of Japanese Patent Application No. 2012-205561, filed Sep. 19, 2012, the contents of which are incorporated herein by reference into the subject application.

TECHNICAL FIELD

The present invention relates to the formation and use of a neuron network, and to a neuron seeding device. More specifically, the invention relates to a culturing device for formation of a neuron network, that through culturing forms a neuron network via synaptic junctions between axons of neurons and dendrites of other neurons, and to a method of using the device to form such a neuron network. In addition, the invention relates to high throughput screening technology, planar patch-clamp technology and neuron imaging technology using such a neuron network.

Furthermore, the invention relates to a neuron seeding device for efficient seeding of neurons in a plurality of selected regions (cell plating sections) of a culturing device for formation of a neuron network or a planar patch-clamp device utilizing the culturing device.

According to the invention, the term "neuron" includes, firstly, various types of neurons such as central neurons and peripheral neurons. The neurons are preferably in a state yet without axonal or dendritic processes. The term "neuron" also encompasses, secondly, cells capable of differentiating into neurons, such as iPS cells and ES cells, and more preferably neural stem cells that are en route to differentiation to neurons from iPS cells or ES cells. In addition, the term "neuron" includes, thirdly, cells having a property of forming an intracellular network, and cells capable of differentiating into cells having a property of forming an intracellular network.

Also, the term "neuronal cell body" refers to the cell body section excluding the processes such as the axons and dendrites of the neuron.

Furthermore, the terms "selected region" and "cell plating section" refer to the region on a plate in which there are set the neurons which are to be the center of neuron network formation, or the target of current/voltage application for ion channel current measurement or various types of imaging, and "selected cells" refers to the neurons in the selected region (cell plating section).

BACKGROUND ART

For the purpose of research or for practical use, the prior art has proposed keeping neurons in culture medium (particularly liquid medium) to construct neuron networks in vitro, with the neurons in a live state.

In NPL 1, for example, there is described formation of a region surrounded by a plurality of protrusions on a Si plate bearing a transistor, as shown in FIG. 2, placement of a large ganglion, as an aggregate of peripheral neurons, of *L. stagnalis*, therein and detection of variations in the potential of the neurons. Also, NPL 2 discloses a neurochip wherein a plurality of roughly circular enclosures known as "cages" (approximately 9 μm height) such as shown in FIG. 3, are formed on a plate, neurons are situated in the space at the center section of each cage, and the axons of neurons are caused to elongate toward neurons in adjacent cages, through several tunnels provided in the cage.

CITATION LIST

Non-Patent Literature

NPL 1: G. Zeck, et al., PNAS 98 (2001) 10457-10462
NPL 2: J. Erickson, et al., J. Neurosci. Methods, 175 (2008) 1-16

DISCLOSURE OF THE INVENTION

Problems to be Solved by the Invention

According to research by the present inventors, the following problems are encountered when forming neuron networks using mammalian neurons, for example.

That is, in order to construct a neuron network having a satisfactory network-like form, it is necessary to plate the neurons in the prescribed selected region (the regions that are to constitute the node points of the network). However, mammalian neurons in a live state in liquid medium are active and can potentially migrate in a random fashion, requiring restrictions on their migration.

Nevertheless, a problem has been encountered when using a structure such as shown in FIG. 1, for example, wherein circular recesses (5 μm depth) connected by narrow grooves to guide elongation of axons on the plate are provided and neurons are placed in the recesses, in that while this restricts migration of the neurons, most of the neurons situated in the recesses die after 2 to 3 days, making it impossible to form a satisfactory neuron network.

This problem is explained by the presumption that neurons are highly sensitive to the culturing conditions and the conditions near the cells, and that for formation of a neuron network it is necessary to facilitate recognition of adjacent neurons by each other. In the experimental structure described above, each of the neurons are accommodated in a recess, and it is difficult for the cells to recognize each other because of the level difference of 5 μm at the plate surface between the adjacent neurons. This is assumed to be the reason that formation of a neuron network is inhibited, the death rate of neurons is increased and the synapse formation is underdeveloped.

NPL 1 places nerve tissue in a region surrounded by a plurality of protrusions, but the object is the giant ganglion of *L. stagnalis* that does not have active mobility. Also, the gaps between the plurality of protrusions easily exceed 50 μm, and it is completely impossible to restrict ordinary neuronal migration. Furthermore, the structure is on a transistor plate with numerous irregularities having heights exceeding 5 μm.

Next, in NPL 2, the neurons in each cage are mutually surrounded by irregular structures known as "cages", each having a height of approximately 9 μm. In addition, while the cage is provided with tunnels having a width of 10 μm and a height of 1 μm for axon elongation, it is difficult for neurons in the cages to mutually recognize adjacent neurons through such narrow tunnels. Therefore, NPLs 1 and 2 do not solve the problems alluded to above, nor do they suggest a solution means.

Methods of forming neuron networks based on application of high throughput screening are important techniques in terms of how neuron seeding is accomplished. For example, when a network is formed having 100 measurement points, with 25 points of cell plating sections surrounding each of the measurement points, this requires seeding of a prescribed number of neuronal cell bodies in a short period of time, usually within 1 hour, at a total of 2500 cell plating sections.

However, NPLs 1 and 2 do not disclose a neuron seeding system for efficient seeding of neurons at multiple cell plating sections. Also, in a method wherein a tool such as an ordinary pipette or a pipette with a metrological function, or a microinjector, is used to seed neurons in individual cell plating sections by manual operation, firstly, it is difficult to accomplish proper seeding in fine cell plating sections and secondly, the seeding efficiency is extremely inferior, and therefore such a method is non-realistic.

A demand therefore exists for a device for neuron seeding that allows seeding of cells without damage in multiple cell plating sections in a short period of time, and in an essentially simultaneous manner. The device must be constructed in such a manner as to not inhibit formation of a neuron network in the planar direction of the apparatus plate.

It is therefore a first object of the present invention to provide a culturing apparatus for formation of a neuron network and a method of forming a neuron network, that can solve the problems mentioned above. It is a second object of the invention to provide a planar patch-clamp device, a high throughput screening technique and a neuron imaging technique utilizing the neuron network.

Furthermore, it is a third object of the invention to provide a neuron seeding device for efficient seeding of neurons in a plurality of cell plating sections of a culturing device for formation of a neuron network or a planar patch-clamp device utilizing the culturing device.

Means for Solving the Problems (Construction of First Invention)
The construction of the first invention designed to solve the aforementioned problems is a culturing device for formation of a neuron network, wherein cell plating sections surrounded by a plurality of protrusions are formed on a flat plate that can be filled with a cell culture medium, the cell plating section satisfying the following conditions (1) to (3).

(1) gaps are set between the plurality of protrusions which defines the cell plating sections, wherein the gaps are wide but do not allow a neuronal cell body to pass through.

(2) the inner diameter of the cell plating sections defined by the plurality of protrusions is of sizes capable of accommodating one to several neuronal cell bodies. The term "several" means 2 to 10, preferably 2 to 6 and more preferably 3 to 5.

(3) the plate surface forming the bottom of each cell plating section comprises at least one constituent of the following (a) and (b).

(a) It is coated with an extracellular matrix-forming substance.

(b) fine through-holes for suction of medium by a an aspirator provided below the plate surface are provided, wherein the hole diameters being such that the neurons cannot pass through.

For the first invention, the phrase "one to several neuronal cell bodies" means at least one and no more than 10, and preferably at least one and no more than 5 neuronal cell bodies.

(Construction of Second Invention)
The construction of the second invention designed to solve the aforementioned problems is a culturing device for formation of a neuron network, wherein the culturing device of the first invention corresponds to any one of the following (1) to (3).

(1) cell plating sections are formed as selected regions on the plate, and one to several neurons are placed in the cell plating sections as the selected cells for the cell plating sections, while other neurons are simply seeded on the plate.

(2) multiple cell plating sections are formed on the plate with appropriate gaps between them, and one to several neurons are placed in the cell plating sections while one cell plating section is used as a selected region in which the neuron is placed.

(3) a culturing device for high-throughput analysis of a neuron network, wherein the cell plating sections are dispersed at appropriate locations so that several or many units of neuron networks corresponding to (1) or (2) can be formed on the plate.

The second invention will now be explained based on the conceptual drawings FIG. 4(a) and FIG. 4(b). FIG. 4(a) shows an essential portion plan view of the plate of a culturing device according to (1) of the second invention, wherein the neuron 11 shown at the center (actually one to several neurons) is situated in a selected region that is the cell plating section 13 surrounded by multiple (6) cylindrical protrusions 12, with the surrounding neurons 11 simply being seeded on the plate. A network is also formed by these neurons 11.

FIG. 4(b), on the other hand, shows an essential portion plan view of the plate of a culturing device according to (2) of the second invention, wherein multiple cell plating sections 13 are formed mutually separated by gaps on the plate in an appropriate manner, a neuron 11 (actually one or more neurons) is situated in each of the cell plating sections 13, and one of the cell plating sections 13 is used as the selected region. A network is also formed by these neurons 11.

In a culturing device according to (3) of the second invention, a plurality of or many neuron network units such as shown in FIG. 4(a) or FIG. 4(b) are dispersed at appropriate locations on the plate, so that they are mutually independent network units.

(Construction of Third Invention)
The construction of the third invention designed to solve the aforementioned problems is a culturing device for formation of a neuron network according to the first invention or second invention, the culturing device for formation of a neuron network being a planar patch-clamp device designed for a neuron network, wherein:

(1) the plate is an electrical insulating plate, wherein fine through-holes are formed so as to pass through both sides of the plate surface which compose the bottom of the cell plating section of the electrical insulating plate, (2) liquid pool sections and electrode sections are provided on the neuron network-formed side, as the first surface side of the fine through-holes, and on the second surface side which is the opposite side, respectively, wherein the liquid pool sections that are to hold the conducting liquid as the cell culture medium, and the electrode sections are disposed to be electrically conductive to the conducting liquid of the liquid pool section, and (3) the liquid pool sections on the first surface side are liquid pool sections for neurons plated in the cell plating sections.

(Construction of Fourth Invention)
The construction of the fourth invention designed to solve the aforementioned problems is a culturing device for formation of a neuron network, wherein in a planar patch-clamp device according to the third invention, the electrode sections on the first surface side and second surface side comprise the following constituents (a) to (c).

(a) an electrode receptacle, wherein at least a portion of the receptacle wall that is in contact with the conducting liquid, when the conducting liquid is introduced into the liquid pool sections, is composed of an inorganic porous material.

(b) an electrode having a precious metal chloride (NmCl) layer formed on a surface layer section of the precious metal (Nm), and housed in the electrode receptacle.

(c) an electrode solution filled into the electrode receptacle, wherein the precious metal chloride (NmCl) and an alkali metal chloride are dissolved at saturated concentration.

(Construction of Fifth Invention)

The construction of the fifth invention designed to solve the aforementioned problems is a culturing device for formation of a neuron network according to any one of the first invention to fourth invention, wherein the culturing device for formation of a neuron network is used for a purpose according to any one of the following (A) to (C).

(A) Use for measurement and analysis of neuronal ion channel current in a neuron network.

(B) Use for imaging analysis, including at least Ca imaging analysis, imaging analysis with synaptophysin or synapsin labeling as synaptic site markers, imaging analysis with MAP2 as a dendrite marker, and imaging analysis with FM1-43 or FM4-64 which labels endosomes or exosomes.

(C) Use in high throughput screening systems for neuron networks.

(Construction of Sixth Invention)

The construction of the sixth invention designed to solve the aforementioned problems is a culturing device for formation of a neuron network according to the fifth invention wherein, when the culturing device for formation of a neuron network is to be used for imaging analysis according to (B), the culturing device comprises one or more of the following constituents (D) to (F).

(D) a photodetector for detecting light emitted by neurons is set above the plate.

(E) an irradiating device that irradiates light onto the neurons or plate surface is set above the plate.

(F) the irradiating device of (E) is equipped with an optical focusing system for irradiation of light only on a prescribed single neuron.

(Construction of Seventh Invention)

The construction of the seventh invention designed to solve the aforementioned problems is a method of forming a neuron network under culturing for any desired research purpose, by means of a culturing device for formation of a neuron network according to any one of the first invention to sixth invention.

The method of forming a neuron network comprises:

(1) a step of seeding neurons on said flat plate that is filled with cell culture medium, (2) a step of placing and/or plating one or several neurons in each cell plating section by an extracellular matrix-forming substance in the cell plating section, and/or by suctioning liquid medium from the fine through-holes at the bottom of the cell plating section, and (3) a step of forming synaptic junctions between neurons by axons or dendrites, wherein while movement of the neurons plated in the cell plating section is restricted by the plurality of protrusions, the presence of mutually adjacent neurons is recognized across the gap sections of the plurality of protrusions.

(Construction of Eighth Invention)

The construction of the eighth invention designed to solve the aforementioned problems is a method of forming a neuron network under according to the seventh invention, wherein during seeding of the neurons in step (1), glial cells are also seeded at sections other than the cell plating sections.

(Construction of Ninth Invention)

The construction of the ninth invention designed to solve the aforementioned problems is a neuron seeding device for seeding of neurons in multiple cell plating sections each surrounded by a plurality of protrusions on the apparatus plate, wherein the neuron seeding device is set on the flat apparatus plate that can be filled with cell culture medium in a culturing device for formation of a neuron network or in a planar patch-clamp device utilizing such a culturing device, wherein a board-shaped device body that can be set on the apparatus plate has a size covering the multiple cell plating sections and the flat bottom of the device body is in contact with the apexes of the plurality of protrusions at the multiple cell plating sections, the device body is provided with (1) a suspension supply port for externally supplying of a neuron suspension having neurons suspended at a fixed density, (2) a plurality of fine suspension flow channels extending in a branched manner from the suspension supply port, inside the device body, and (3) a suspension injection port for injecting of neuron suspension into each cell plating section, opened at the bottom of the device body at the end of each suspension flow channel.

(Construction of Tenth Invention)

The construction of the tenth invention designed to solve the aforementioned problems is a neuron seeding device according to the ninth invention, wherein the plurality of suspension flow channels are set to have substantially the same lengths, and the design is such that when the neuron seeding device is placed on the apparatus plate of the culturing device for formation of a neuron network or the planar patch-clamp device, the individual suspension injection ports are located to precisely correspond with the individual cell plating sections.

(Construction of Eleventh Invention)

The construction of the eleventh invention designed to solve the aforementioned problems is a neuron seeding device according to the ninth invention or tenth invention, wherein the board-shaped device body comprises an upper board provided with the suspension supply ports and a lower board provided with the suspension injection ports, joined in a closely bonded state, with grooves composing the suspension flow channels being formed on at least one of the bonding surfaces of the upper board and lower board.

(Construction of Twelfth Invention)

The construction of the twelfth invention designed to solve the aforementioned problems is a neuron seeding device according to any one of the ninth invention to eleventh invention, wherein the culturing device for formation of a neuron network is a culturing device for formation of a neuron network according to the first invention, and/or the planar patch-clamp device according to any one of the ninth invention to eleventh invention is a planar patch-clamp device according to the third invention.

(Construction of Thirteenth Invention)

The construction of the thirteenth invention designed to solve the aforementioned problems is a neuron seeding device according to any one of the ninth invention to twelfth invention, wherein the device body further comprises second suspension flow channels for injection of the neuron suspension into regions other than the cell plating sections of the apparatus plate of the culturing device for formation of a neuron network or the planar patch-clamp device.

Effect of the Invention (Effect of the First Invention)

The culturing device for formation of a neuron network of the first invention comprises cell plating sections surrounded by a plurality of protrusions, formed on a flat plate, and therefore the neurons placed therein have their random movement restricted by the plurality of protrusions. Random movement of the neurons is therefore restricted.

However, the insides and outsides of the cell plating sections are on the same flat plate surface, with no level differences (irregularities) between them. Furthermore, wide gaps are set between the plurality of protrusions of the cell plating sections, though not wide enough to allow passage of the neuronal cell bodies, and the gap sections are spaces that are open above, instead of narrow tunnel spaces such as disclosed in NPL 2. Consequently, the neurons situated in the cell plating sections can easily recognize adjacent neurons with which they are to form a network, and it is possible to create a satisfactory neuron network based on formation of synaptic junctions between axons and dendrites utilizing the gaps between the protrusions.

In addition, since the inner diameters of the cell plating sections defined by the plurality of protrusions have sizes allowing accommodation of one to several neuronal cell bodies, one to several neuronal cell bodies are situated and plated in each cell plating section. Generally speaking, neurons (especially iPS cells and the like) can survive more stably for longer periods when in a state of aggregates of several cells (clusters). On the other hand, if a single neuron is placed in the cell plating section, signal transfer between neurons will be simplified and analysis of the network function will be easier. According to the first invention, one to several neuronal cell bodies are situated and plated in each cell plating section, thereby creating a satisfactory balance between both of the aforementioned requirements.

When a culturing device for formation of a neuron network according to the first invention is used, neurons can survive for long periods of 4 weeks or longer, and an active neuron network can be maintained.

Furthermore, according to the first invention, an extracellular matrix exhibiting adhesive force for neurons is coated onto the plate surface composing the bottom of the cell plating section, and/or fine through-holes for suction of cell culture medium by an aspirator provided below the plate are provided with hole diameters that do not allow passage of neurons. Thus, one to several neuronal cell bodies are securely situated and plated in the cell plating sections that are to serve as nodes of the mesh-like neuron network. With these features, the first invention can solve the aforementioned problems of the invention.

(Effect of the Second Invention)

According to the second invention there is provided a culturing device for formation of a neuron network, used to form a neuron network as shown in FIG. 4(a) or a neuron network as shown in FIG. 4(b), and a plurality or many of such neuron network units may be formed on the plate. Thus, a culturing device for high-throughput analysis of a neuron network is provided.

(Effect of the Third Invention)

A planar patch-clamp device allows multipoint measurement by constructing a plurality of patch-clamp devices on a solid plate having electrical insulating properties, such as a silicon chip, and it has fine through-holes for measurement of ion channel current at each of the cell placement locations of each patch-clamp device. In a planar patch-clamp device of the third invention, the "fine through-holes for suction of cell culture medium by an aspirator provided below the plate", as specified by (3)(b) of the first invention, are used as fine through-holes for measurement of the ion channel current.

Also, a substance such as adenosine 5-[β-thio]diphosphate, uridine 5-triphosphate trisodium salt hydrate or EGF, which has a neuron-attracting effect, may be mixed with the cell culture medium on the second surface side to attract neurons into the cell culture medium on the second surface side, thereby guiding the neurons to the fine through-holes to more reliably keep the neurons in the fine through-holes during the culturing period.

Since a conventional planar patch-clamp device does not have a cell culturing function, a problem has been encountered in that it has not been applicable for cells that require culturing, such as neurons. In other words, because the lifetime of cells to be measured is as short as 1 hour or even 30 minutes or less under non-culturing conditions, the device only has limited application for innovative drug screening, and it has been difficult to apply for functional analysis of cells wherein a pipette patch clamp is employed. In addition, it has been difficult to successfully carry and trap cells at the locations of the fine through-holes provided in the plate.

According to the third invention, however, a culturing device for formation of a neuron network according to the first invention or the second invention is used as a planar patch-clamp device for a neuron network, so that a planar patch-clamp device can be provided that is designed for a neuron network of neurons that require culturing, and that results in a notably extended lifetime for the neurons to be measured. Furthermore, by using a culturing device for formation of a neuron network specified by (3) of the second invention, it is possible to accomplish high-throughput screening in a neuron network.

(Effect of the Fourth Invention)

Incidentally, the following issue arises with a planar patch-clamp device according to the third invention.

Specifically, when an extracellular matrix-forming substance is adhered to the peripheries of the fine through-holes for measurement of ion channel current (the cell plating sections), as according to (3)(a) of the first invention, a slight gap is formed between the neuronal cell membrane and the plate surface at each fine through-hole periphery, thereby lowering the "seal resistance". The current flowing through this gap is added as leak current to the ion channel current, and fluctuations therein contribute to noise. When the seal resistance is lowered, therefore, noise current becomes significant even with respect to slight fluctuations in the applied membrane potential, and it becomes difficult to accurately measure the ion channel current.

For accurate measurement of cellular ion channel current it is effective and essential to counter noise current not only when the seal resistance of the planar patch-clamp device is low but also when the seal resistance is not low. Effective measures against noise current include not only increasing the seal resistance but also minimizing fluctuations in the applied membrane potential at the electrode side.

Furthermore, when the planar patch-clamp device electrode used is an electrode having a precious metal chloride (NmCl) layer (for example, an AgCl layer) formed on the surface layer section of the precious metal Nm (for example, silver Ag), fluctuations in the applied membrane potential are mainly due to fluctuations in the interface potential between the surface of the AgCl/Ag electrode and the solution surrounding it, or fluctuations in the liquid-liquid interface potential.

Thus, by dipping an AgCl/Ag electrode in an electrode solution which is a saturated solution of AgCl and an alkali metal chloride (for example, KCl) (the KCl concentration being about 100-150 millimoles) in the electrode receptacle of the electrode section, and contacting these with a conducting liquid such as a cell culture solution (the KCl concentration being about a few millimoles) through the receptacle wall formed of an inorganic porous material, as according to the fourth invention, the interior and exterior of the electrode receptacle are brought to an electrically conductive state. However, since the liquid itself cannot appreciably pass through the pores of the inorganic porous material, mixture of the electrode solution in the electrode receptacle with the conducting liquid outside the electrode receptacle is minimal enough to ignore. As a result, a constant and large difference in KCl concentration is maintained between the interior and exterior of the electrode receptacle, the AgCl/Ag electrode interface potential and the liquid-liquid interface potential are constant, and fluctuations in the applied membrane potential do not occur.

(Effect of the Fifth Invention)

According to the fifth invention, a culturing device for formation of a neuron network according to the first invention to fourth invention may be used for (A) measurement and analysis of the neuronal ion channel current in the neuron network, (B) imaging analysis that includes at least Ca imaging analysis, imaging analysis with synaptophysin or synapsin labeling as synaptic site markers, imaging analysis with MAP2 as a dendrite marker, and imaging analysis with FM1-43 or FM4-64 which labels endosomes or exosomes, or (C) a high throughput screening system for a neuron network.

(Effect of the Sixth Invention)

According to the sixth invention, when a culturing device for formation of a neuron network according to the fifth invention is used for imaging analysis according to (C), because it further comprises one or more elements from among (D) a photodetector, (E) an irradiating device and (F) an optical focusing system, effects are obtained such as, firstly, that it is possible to accomplish analysis without inhibiting the neuron network function, since measurement can usually be carried out in a non-contact and non-destructive manner, secondly, that the optical measurement allows analysis at high speed, and thirdly, that it is possible to exactly excite a single neuron and precisely analyze it with the (F) optical focusing system, even when multiple neurons (cell clusters) are situated in the cell plating section.

(Effect of the Seventh Invention)

According to the method of forming a neuron network according to the seventh invention, steps (1) to (3) mentioned above are carried out using a culturing device for formation of a neuron network according to any one of the first invention to sixth invention.

Thus, when neurons are seeded on a flat plate filled with cell culture medium, the extracellular matrix-forming substance in each cell plating section, or suction of cell culture medium through the fine through-holes at the bottom of the cell plating section, allows one to several neuronal cell bodies to be reliably placed and plated in the cell plating section. More specifically, cell bodies may be placed and plated on the fine through-holes of the cell plating section.

In addition, since the inner diameter of each cell plating section roughly corresponds to a size allowing accommodation of one to several neuronal cell bodies, one to several neurons are reliably situated in each cell plating section. These neurons have their random movement restricted by the plurality of protrusions forming the cell plating section. Furthermore, since the inside and outside of the cell plating section are on the same flat plate surface and there is no level difference (irregularities) between them, the neurons disposed on the cell plating section can easily recognize adjacent neurons that are to form the network, through the gaps between the plurality of protrusions composing the cell plating section. Thus, the neurons can be kept in an actively live state while forming a satisfactory neuron network based on formation of synaptic junctions between axons and dendrites utilizing the gaps between the protrusions.

Given these aspects, the seventh invention allows formation of a satisfactory neuron network between individual neuron clusters of several neurons placed and plated in each cell plating section. With this method, the neurons form a stable network with approximately 100% probability, and culturing can be continued for prolonged periods of 4 weeks and longer. It is therefore a highly useful technique for producing a high throughput screening element for a neuron network.

(Effect of the Eighth Invention)

According to the eighth invention, when neurons are seeded by step (1) of the seventh invention, the neurons are seeded both inside the selected regions and outside the selected regions while glial cells are seeded outside the selected regions. Thus, since glial cells are present near the synapse and in contact with the neurons, as known from publications such as "F. W. Pfrieger et al., Science 277 (1997) 1684-1687", this increases maturation of the neuron network and allows construction of a neuron network with a more homogeneous spatio-temporal function.

(Effect of the Ninth Invention)

According to the ninth invention there is provided a neuron seeding device for efficient seeding of neurons in multiple cell plating sections of a culturing device for formation of a neuron network or a planar patch-clamp device utilizing the culturing device. Thus, for formation of a neuron network based on application of high throughput screening, there is provided means for solving the important issue of how the neuron seeding is accomplished.

The board-shaped device body of the device comprises (1) a suspension supply port for external supply of a neuron suspension, (2) a plurality of fine suspension flow channels extending in a branched fashion from the suspension supply port, and (3) a suspension injection port opened at the bottom of the device body at the end of each suspension flow channel. Thus, even when a large number, in the hundreds, of cell plating sections are provided on the apparatus plate, it is possible to supply the neuron suspension to all of the cell plating sections in a short period of time.

The method of supplying the neuron suspension to the suspension supply port is not restricted, but in consideration of fluid friction resistance in the multiple fine suspension flow channels, supply of the neuron suspension is preferably carried out with a tool or device allowing injection of liquid into the suspension supply port (for example, an injector or microsyringe, or a small pump-type injector), under a pressurized state. Since in most cases the size of the injection port of the tool or device for liquid injection will be larger than the inner diameter of the suspension supply port, in such cases a connecting pipe with a tapered tip end may be fitted at the injection port of the liquid inject tool/device, allowing the tapered tip end to be inserted into the suspension supply port. The tapered section of the tip end of the connecting pipe may be provided by fitting a small stainless steel nozzle-shaped pipe member, for example.

The neurons injected into the cell plating section have their flow out of the cell plating section halted by the plurality of protrusions of the cell plating section, and therefore stop within the cell plating section. On the other hand, the suspension medium flows out between the plurality of protrusions of the cell plating section. Consequently, the neurons are seeded into the cell plating section in an intact state with minimal stress. Furthermore, since seeding of the neurons is accomplished all at once, seeding of the neurons in the multiple cell plating sections on the apparatus plate is completed essentially simultaneously, and within a very short period of time (about several tens of seconds).

Also importantly, the neuron seeding device is setup in the culturing device for formation of a neuron network or the planar patch-clamp device, on a flat apparatus plate that can be filled with cell culture medium. Thus, the construction is such that the neuron suspension is injected from above the cell plating section. Consequently, there is no hindrance to formation of a neuron network in the planar direction on the apparatus plate.

Incidentally, while it is possible to anchor the neuron seeding device on the apparatus plate of the culturing device for formation of a neuron network or the planar patch-clamp device, if it is set in a detachable manner and removed after seeding of the neurons, it will not impede supply of oxygen or carbon dioxide gas during culturing of the seeded neurons and will not interfere with measurement of the network or introduction of chemical solution from above.

(Effect of the Tenth Invention)

According to the tenth invention, the multiple suspension flow channels are set to substantially the same length, and therefore seeding of the neurons in the multiple cell plating sections on the apparatus plate is completed accurately and simultaneously. Stated differently, if the liquid volume of the neuron suspension supplied from the suspension supply port is controlled after adjusting the dispersion density of the neurons of the neuron suspension on the nodes, an effect is obtained whereby the injection rate of neuron suspension into the cell plating section (and therefore the number of neurons seeded) can be controlled in essentially a precise manner, and whereby the number of neurons seeded in the multiple cell plating sections can be controlled to be essentially equal. These effects may be considered to be major effects for forming a neuron network that is presumably to be used for high throughput screening.

Also, since the design is such that when the neuron seeding device is placed on the apparatus plate of the culturing device for formation of a neuron network or the planar patch-clamp device, the individual suspension injection ports are located to precisely correspond with the individual cell plating sections, seeding of neurons in the multiple cell plating sections is accomplished in a precise manner. In this regard, when the neuron seeding device is placed on the apparatus plate of the culturing device for formation of a neuron network or the planar patch-clamp device, the labeling marks for positioning of both may be provided on either or both the apparatus plate and device body, and it is particularly effective when the device body is made of a highly transparent material since this will allow such labeling marks to be visible through it.

(Effect of the Eleventh Invention)

According to the eleventh invention, the board-shaped device body has an upper board provided with a suspension supply port and a lower board provided with a suspension injection port, with grooves forming suspension flow channels in at least one of the bonding surfaces of the boards, thus facilitating the working steps for forming numerous fine, curved suspension flow channels inside the device body. However, the method of working to form the suspension flow channels is not limited to the one described here.

(Effect of the Twelfth Invention)

According to the twelfth invention, there are provided specific and preferred embodiments of neuron seeding devices, wherein the culturing device for formation of a neuron network is one according to the first invention, and/or the planar patch-clamp device is one according to the third invention.

(Effect of the Thirteenth Invention)

When neurons have been seeded only in the cell plating sections of the apparatus plate of the culturing device for formation of a neuron network or the planar patch-clamp device, a neuron network is not satisfactorily formed in most cases because of an insufficient overall number of individual neurons in the apparatus plate. In order to solve this problem, the device body of the thirteenth invention further comprises second suspension flow channels for injection of a neuron suspension into regions other than the cell plating sections of the apparatus plate. Since it is thus possible to seed neurons by appropriately injecting a neuron suspension into regions other than the cell plating sections of the apparatus plate, the neuron network can be formed in a particularly satisfactory manner.

BEST MODE FOR CARRYING OUT THE INVENTION

Figure 1:
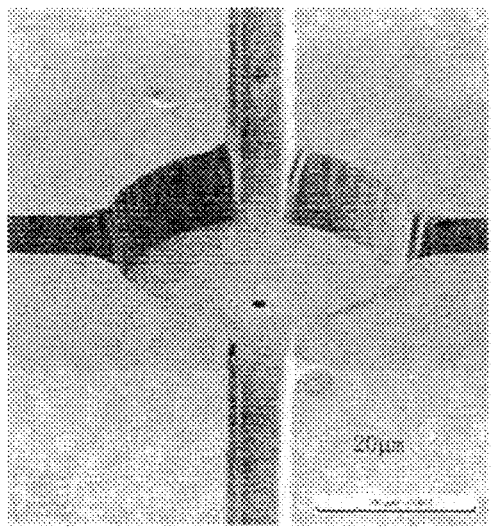
FIG. 1 shows a recess structure on a plate prepared as a prototype by the present inventors (prior art comparative example).
Figure 2:
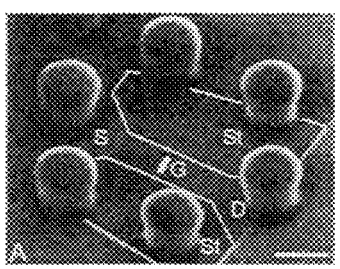
FIG. 2 shows the structure on a Si plate as disclosed in prior art NPL 1.
Figure 2:
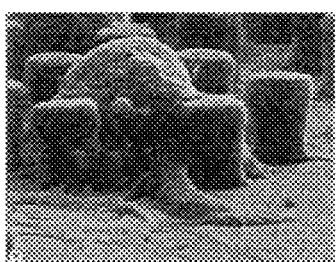
Figure 3:
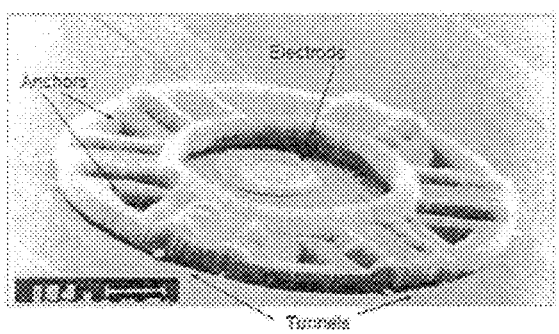
FIG. 3 shows the structure of the cage disclosed in prior art NPL 2.
Figure 4:
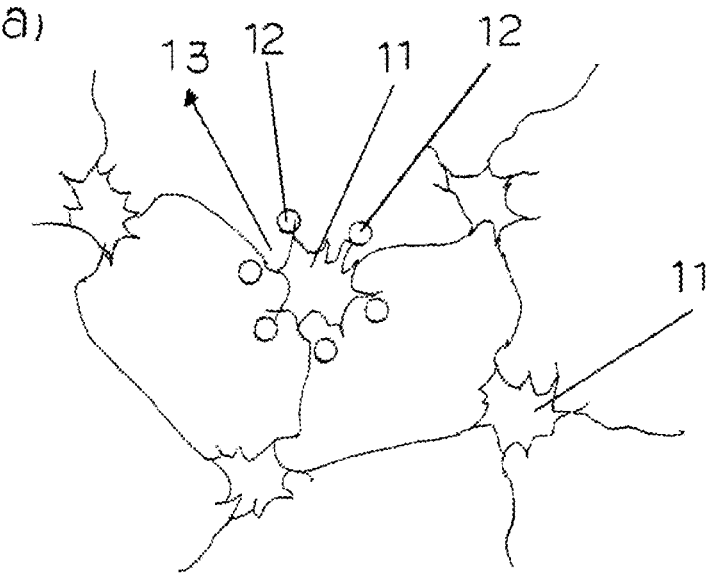
FIG. 4 is a pair of plan views conceptually showing the essential portions of a culturing device for formation of a neuron network according to (1) and (2) of the second invention.
Figure 4:
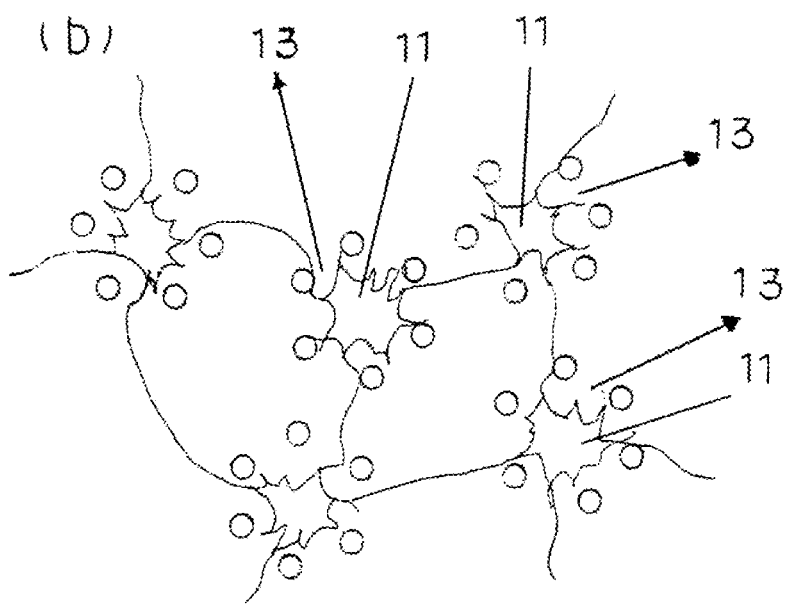

Embodiments of the invention will now be explained, including their best modes. The technical scope of the invention is not limited by these embodiments.

Technical Field of the Invention

The technical field of the invention is the technical field of forming a neuron network while culturing neurons in a stable condition. Also, it is the technical field of measuring ion channel current on cell surfaces. It is additionally the field of stimulating cells by injecting current or applying voltage. It is yet further the field of high throughput screening technology of the type involving measurement of ion channel current or stimulating cells by injecting current or applying voltage. It is still yet further the field of Ca imaging or various other types of imaging techniques designed for neurons or neuron networks.

[Neurons and Neuron Networks]

Neurons comprise cell bodies that are the main bodies of the cells, and axons and dendrites that elongated from the cell bodies. There are no restrictions on the type of neurons, but firstly there may be mentioned neurons such as central neurons or peripheral neurons, and most preferably neurons in a state before processes such as axons and dendrites have developed. Secondly, there may be mentioned cells capable of differentiating into neurons, such as iPS cells and ES cells, and more preferably neural stem cells that are en route to differentiation to neurons from iPS cells or ES cells. Thirdly, there may be mentioned cells having a property of forming an intracellular network, and cells capable of differentiating into cells having a property of forming an intracellular network. The neurons are preferably animal neurons, and most preferably neurons of mammals, which include humans. The sizes of the cell bodies of the neurons will usually be less than 20 µm, and more specifically are about 3 to 18 µm.

The neuron network has as its basic structural unit a pair of neurons, namely a trigger cell that emits a signal and a follower cell that receives it. The present inventors have found that when the difference in the heights on the surface on which the trigger cells and follower cells are present is about the size of the cells, the cell death rate increases.

[Culturing Device for Formation of Neuron Network]

In the culturing device for formation of a neuron network according to the invention, cell plating sections are formed by a plurality of protrusions, on a flat plate that can be filled with a cell culture medium (most preferably a liquid medium).

The "flat plate that can be filled with a cell culture medium" has the construction described for the planar patch-clamp device described below, for example. The cell plating sections are a plurality or many set on the plate according to the structure of (1) to (3) of the second invention. However, since the base unit in the neuron network is a pair of neurons consisting of a trigger cell and a follower cell, when the structure is such that spontaneous firing of a neuron is the trigger and ion channel current is received by the follower cell, a cell plating section as the selected region can operate as a functional analysis element even at a single location. The mutual gaps between the cell plating sections as the selected regions will differ depending on the type of neuron network and cannot be specified for all cases, but they may be about 50 to 500 µm, for example.

The shapes of the plurality of protrusions forming the cell plating section are not restricted, but are preferably fence-shaped or post-shaped, for example. The heights of the protrusions are also not restricted, but they are generally preferred to be heights of about 10 µm to effectively restrict random movement of the neurons, and for example, for mouse cerebral cortex or hippocampal neurons they are preferably heights of about 5 to 10 µm.

The cell plating section satisfies the following conditions (1) to (3).

(1) Gaps are set, between the plurality of protrusions forming the cell plating sections, which are wide but do not allow a neuronal cell body to pass through. The protrusion gaps are determined according to the sizes of the mammalian neuronal cell bodies, which vary within about 3 to 18 µm, and it is difficult to specify an absolute value for all cases. As one reference point, if the cell body size is represented as X µm, the upper limit for the gaps is preferably no greater than 0.9X µm and especially no greater than 0.7X µm, and the lower limit for the gaps is preferably at least 0.3X µm and especially at least 0.5X µm. When the top ends of the plurality of protrusions are preferably not connected to each other as this will essentially form a tunnel structure. Synapse formation may occur in the tunnels of a tunnel structure, but imaging of such synapses is not possible.

(2) The inner diameters of the cell plating sections formed by the plurality of protrusions are of sizes capable of accommodating one to several neuronal cell bodies. The inner diameters of the cell plating sections are appropriately set according to the sizes of the neuronal cell bodies and the number of cell bodies in the cell plating section. For example, if the cell body in each cell plating section is a single mammalian neuronal cell body, the inner diameter of each cell plating section is preferably about 10 to 25 µm. If the inner diameter of the cell plating section is excessively greater than the size of the cell body, too many cell bodies may become situated in a single selected region, while if the inner diameter of the cell plating section more than 50% smaller than the size of the cell body, it may not be possible for the cell body to be stably situated in the cell plating section.

(3) The plate surface forming the bottom of each cell plating section comprises at least one element of the following (a) and (b).

(a) It is coated with an extracellular matrix-forming substance.

(b) There are provided fine through-holes for suction of medium by an aspirator provided below the plate surface, the hole diameters being such that the neurons cannot pass through.

Of these conditions for (3), the (a) extracellular matrix-forming substance is one that exhibits adhesive force for neurons in order to plate the neurons at the bottom of the cell plating section, and examples for the constituent materials include polylysine, collagen (type I, type I and type IV), fibronectin, laminin, proteoglycan, (versican, decholin and the like), proteoglycan (aggrecan), link proteins, entactin, tenascin, proteoglycans [chondroitin sulfate proteoglycan, heparan sulfate proteoglycan (perlecan and the like), keratan sulfate proteoglycan and dermatan sulfate proteoglycan], hyaluronic acid (a type of glycosaminoglycan), elastin, fibrin, gelatin, Matrigel, and the like.

The fine through-holes for suction of cell culture medium specified by (b) allow suctioning of cell culture medium with an aspirator on the lower side of the plate, thereby plating the one to several neurons situated in the cell plating section onto the bottom of the cell plating section, the hole diameters being of a size that the neurons do not pass through, such as about 1 to 3 µm.

[Planar Patch-Clamp Device]

One example of effective use of the culturing device for formation of a neuron network is as a planar patch-clamp device for a neuron network.

(Common Planar Patch-Clamp Device)

Several different membrane proteins are arranged on the surface of cells composing an organism, and binding of chemical substances (signal transfer substances such as ligands) to specific sites on the cell surface or electrical or optical stimulation (gate trigger) opens and closes the channels serving as openings for membrane proteins, to control transport of ions and chemical substances between the outside and inside of the cell membrane. The ion channels that carry out this control are membrane proteins that are important for biological signal transfer, and measurement of electrical changes in channel proteins, i.e. ion channel current, is one of the goals for functional measurement and development of function-related chemicals.

The need to meet this goal has led to the development of techniques that employ pipette patch clamps, planar patch-clamps and the like. Pipette patch clamps have a drawback in that they cannot be applied to high throughput screening by multipoint measurement. In contrast, a planar patch-clamp is a flat plate-like patch-clamp device that allows multipoint measurement of cell ion channel current by constructing a plurality of patch-clamp devices on a solid plate such as a silicon chip, and it has fine through-holes for measurement of ion channel current at each of the cell placement locations of each patch-clamp device.

However, since a common conventional planar patch-clamp device does not have a cell culturing function, a problem has been encountered in that it has not been applicable for cells that require culturing, such as neurons. In other words, because the lifetime of cells to be measured is as short as 1 hour or even 30 minutes or less under non-culturing conditions, the device only has limited application for innovative drug screening, and it has been difficult to apply it for functional analysis of cells wherein a pipette patch clamp is employed. In addition, it has been difficult to successfully carry and trap cells at the locations of the fine through-holes provided in the plate.

(Planar Patch-Clamp Device of the Invention)

In contrast, a planar patch-clamp device of the invention also has a neuron-culturing function, unlike a planar patch-clamp device with a common construction as described above, and it allows effective minimization of noise current during ion channel current measurement and stable positioning of cells. That is, the characteristic construction of the device is such that cell-anchoring force is applied to the opening for plating of the neuron at the fine through-holes provided on the plate, and a liquid pool section capable of current flow to an electrode is provided on the surfaces on both sides of the through-holes in the plate, the liquid pool section being fillable with a conducting liquid (for example, a cell culture solution). With this planar patch-clamp device, it is possible to easily trap neurons at the locations of the fine through-holes, and to measure ion channel activity over sufficient time under cell culturing conditions.

Specifically, the culturing device for formation of a neuron network in the planar patch-clamp device of the invention is constructed in a manner according to the following (1) to (3).

(1) The plate is an electrical insulating plate, and fine through-holes are provided connecting the surfaces on both sides of the electrical insulating plate.

(2) The neuron network-forming side, as the first surface side of each fine through-hole, and the second surface side on the opposite side, each have a liquid pool section for holding of the conducting liquid, and an electrode section situated so as to allow conduction to the conducting liquid of the liquid pool section.

(3) The liquid pool section of the first surface side is the liquid pool section for the neurons plated in the cell plating section.

(Main Construction of Planar Patch-Clamp Device of the Invention)

In the planar patch-clamp device of the invention, therefore, fine through-holes are provided allowing communication between the first surface side (the surface side on which the cells are placed) and the second surface side, which are both surfaces of the plate with electrical insulating properties.

The plate with electrical insulating properties is preferably a plate made of glass, ceramic, plastic or the like. When a silicon plate is to be used, a preferred example is a silicon plate (SOI plate) having a laminated structure with a silicon layer on the first surface side, a silicon oxide layer in the middle and a silicon layer on the second surface side. Since a silicon plate having such a layered structure has a very highly insulating interlayer present between two silicon layers, it is possible to establish a high resistance state during ion channel closure of the cell being measured, and to reduce background noise.

The number of through-holes in the plate is not particularly restricted, but it is preferably several to many, and for example, two to several dozen, or more. The inner diameters of the fine through-holes are preferably inner diameters such that liquid can pass through but the neurons cannot (for example, about 1 to 3 µm), although there is no restriction to this range for the inner diameters.

Also, both the first surface side and second surface side of the through-holes of the planar patch-clamp device have a liquid pool section for holding of the conducting liquid, and an electrode section situated so as to allow conduction to the conducting liquid of the liquid pool section.

The construction of the liquid pool sections is not restricted so long as it satisfies the condition of "holding the conducting liquid while allowing conduction to the electrode section to the conducting liquid", and they may be formed, for example, by layering a spacer member or plate member on each of the first surface side and second surface side of the plate, and providing notched sections in the spacer member in the regions corresponding to the through-holes of the plate, as shown in the first example.

While not necessarily constituting a restriction, preferably the spacer member and plate member on the first surface side are made of optically opaque materials, and preferably the spacer member and plate member on the second surface side are made of optically transparent materials.

The liquid pool sections are constructed in a fluid-tight manner themselves, while being provided with liquid flow channels or openable/closeable openings for introduction and discharge of a conducting liquid (a conducting liquid that is cell culture medium in which neurons are dispersed). Each liquid pool section on the first surface side of the plate has the top of the liquid pool section covered with a covering member such as cover glass, and if necessary the covering member may be removed to open the liquid pool section.

In the planar patch-clamp device, the first surface side and second surface side are provided with electrode sections having novel constructions, which will be described below under "Electrode section structure in planar patch-clamp device".

Also in the planar patch-clamp device, preferably the liquid pool section on the first surface side has a construction with a main pool for placement of the cells, and a secondary pool in which the electrode section on the first surface side is situated, each formed of an optically opaque material, and a narrow liquid flow channel connecting the pools. Also, the liquid pool section on the second surface side is preferably connected to a liquid flow channel for introduction and discharge of a conducting liquid, with the electrode section on the second surface side being situated in the liquid flow channel.

Furthermore, the liquid pool sections on the first surface side correspond to the selected regions of the neuron. Thus, a plurality or many liquid pool sections on the first surface side are set on the plate with suitable mutual gaps between them in the two-dimensional direction, with cell plating sections being formed surrounded by a plurality of protrusions in each liquid pool section on the first surface side.

Likewise, a plurality of liquid pool sections are also set on the second surface side at locations corresponding to the liquid pool sections on the first surface side, the liquid pool sections on the first surface side and the second surface side being connected by the fine through-holes of the plate. The liquid pool sections on the second surface side are also connected to a liquid suction device, and when negative pressure is applied to the liquid pool section on the second surface side by the liquid suction device, negative pressure is also applied to the liquid pool section on the first surface side through the fine through-holes. The fine through-holes correspond to the fine through-holes for suctioning of cell culture medium at the bottom of the cell plating section described as (b). Also, an extracellular matrix-forming substance with cell-anchoring force is adhered to the periphery of the opening on the first surface side at the fine through-hole. This corresponds to coating of an extracellular matrix-forming substance on the bottom of the cell plating section, described as (a).

[Electrode Section Structure in Planar Patch-Clamp Device]

In the planar patch-clamp device, the electrode sections on the first surface side and second surface side also preferably comprise the following elements (a) to (c).

(a) An electrode receptacle of which at least a portion of the receptacle wall that is to contact with the conducting liquid introduced into the liquid pool section, is composed of an inorganic porous material.

(b) An electrode having a precious metal chloride (NmCl) layer formed on a surface layer section of the precious metal (Nm), housed in the electrode receptacle.

(c) An electrode solution comprising the precious metal chloride (NmCl) and an alkali metal chloride dissolved to saturated concentration, filled into the electrode receptacle.

The type of precious metal Nm in the electrode section structure is not restricted, but is preferably silver Ag or platinum Pt, with silver Ag being especially preferred. Thus, the precious metal chloride NmCl is preferably silver chloride AgCl or platinum chloride PtCl, with silver chloride AgCl being preferred. The alkali metal chloride is also not restricted, but is preferably potassium chloride KCl. The inorganic porous material composing at least a portion of the receptacle wall is preferably porous glass or porous ceramic.

Also, preferably the electrodes of the electrode section satisfy the following (1) or (2).

(1) A rod-shaped electrode protruding in the electrode receptacle, with a precious metal chloride NmCl layer formed on the surface layer section of a core material made of a precious metal Nm.

(2) A tubular electrode formed on the inner peripheral surface of the wall section of the electrode receptacle, the bottom layer on the receptacle wall side being a vapor deposition layer of a precious metal Nm, and the surface layer contacting the electrode solution being a vapor deposition layer of a precious metal chloride NmCl.

[Imaging Analysis Using Culturing Device for Formation of Neuron Network]

A culturing device for formation of a neuron network or planar patch-clamp device according to the invention may be used for various types of imaging analysis, including at least Ca imaging analysis, imaging analysis with synaptophysin or synapsin labeling as synaptic site markers, imaging analysis with MAP2 as a dendrite marker, and imaging analysis with FM1-43 or FM4-64 which labels endosomes or exosomes.

(Ca Imaging Analysis)

Ca imaging is a method in which a Ca probe (a dye that bonds to Ca ion and emits fluorescence) is introduced into a neuron, and inflow of Ca ion into the cell body, when an action potential is generated in the neuron, is captured as fluorescence, and it allows analysis of cellular ion channel current by observing the fluorescence produced during generation of an action potential or during propagation of an action potential.

By thus forming a neuron network using neurons with an introduced Ca probe, and for example, conducting current injection or voltage application to a single neuron within it, it is possible to perform measurement by Ca imaging of a plurality or many neurons.

According to this method, a single neuron of the neuron network (a first neuron) is selected and stimulated by current injection or voltage application to generate an action potential, while simultaneously the action potential is propagated to a surrounding adjacent neuron (second neuron) through the neuron network, and the state of propagation from the second neuron to a third neuron adjacent to it may be measured by Ca imaging.

Electrode stimulation is an example of a prior art method, but with this method it is difficult to selectively stimulate single neurons, and analysis becomes complex. Also, although selective stimulation of single neurons is possible by stimulation using a micropipette electrode, as another prior art method, it is difficult to accomplish multichannel measurement for high throughput screening. The method of the invention allows the measuring device to be greatly downsized to facilitate multichannel measurement.

(Imaging Analysis by Synaptophysin and Synapsin)

Synaptophysin and synapsin are synapse vesicle membrane proteins, used as markers of synaptic sites, and by binding a dye to their antibodies and utilizing antigen-antibody reaction to bind the dyes to these proteins, it is possible to accomplish labeling of synaptic sites.

(Imaging Analysis by MAP2)

MAP2 is a dendrite marker, and adding a dye to its antibody and conducting reaction allows labeling of dendritic sites.

(Imaging Analysis by FM1-43 and FM4-64)

FM1-43 and FM4-64 reversibly enter the cell membrane without passing through the cell membrane, and emit fluorescence only when binding to the cell membrane, and can thus label endosomes and exosomes. They have the feature of allowing labeling while maintaining cellular biological function.

(Optical Systems for Imaging Analysis)

When a culturing device for formation of a neuron network or a planar patch-clamp device according to the invention is used for the various types of imaging analyses mentioned above, the device preferably comprises the following optical system elements.

First, a photodetector for light emitted by neurons is set on the first surface side of the plate of the device. Also, an irradiating device for irradiation of laser light or the like onto the neuron or plate surface is set on the first surface side of the plate of the device. The irradiating device most preferably is also equipped with an optical focusing system to irradiate light only on specified single cells.

By providing such an optical system element it is possible to carry out optical measurement in a non-contact, non-destructive manner, allowing analysis without inhibiting the function of the neuron network, while also allowing high-speed analysis and accurate analysis by excitation of single neurons in a precise manner with an optical focusing system.

[Neuron Seeding Device]

The neuron seeding device of the invention is a device for seeding of neurons in multiple cell plating sections surrounded by a plurality of protrusions on an apparatus plate, where a culturing device for formation of a neuron network or a planar patch-clamp device utilizing the culturing device, is set up on a flat apparatus plate that can be filled with cell culture medium.

The "culturing device for formation of a neuron network" is not limited in its construction so long as it has multiple cell plating sections formed surrounded by a plurality of protrusions on a flat apparatus plate that can be filled with cell culture medium. Likewise, a "planar patch-clamp device" is not limited in its construction so long as it is a device utilizing a culturing device for formation of a neuron network and has multiple cell plating sections formed surrounded by a plurality of protrusions on a flat apparatus plate that can be filled with cell culture medium. Most preferably, however, the "culturing device for formation of a neuron network" is a culturing device for formation of a neuron network of the invention according to the embodiment described above, and the "planar patch-clamp device" is a planar patch-clamp device of the invention according to the embodiment described above.

In a neuron seeding device according to the invention, the device body has a board shape that can be set on an apparatus plate of the culturing device for formation of a neuron network or a planar patch-clamp device. Generally speaking, "board shape" means a sheet-like or thick sheet-like form, and in most cases the planar shape will be quadrilateral (square or rectangular). According to the invention, however, the specific form of the "board shape" is not restricted so long as it is a form that can be set on the apparatus plate of the culturing device for formation of a neuron network or the planar patch-clamp device, and at least the bottom is flat so that the bottom contacts the apexes of the plurality of protrusions at the multiple cell plating sections on the apparatus plate, and so long as the bottom has a size covering the multiple cell plating sections when set on the apparatus plate.

It is convenient if the "board-shaped" device body has a planar shape and size (area) basically corresponding to the apparatus plate of the culturing device for formation of a neuron network or the planar patch-clamp device. The planar shape of the device body is not limited to being quadrilateral, and may be circular, elliptical or some other irregular shape, and the thickness may be from about several mm to several cm, for example. The area of the bottom of the device body preferably corresponds to the area of the apparatus plate, and for example, it may be freely selected from about 2 to 3 $cm^2$ to about several tens of $cm^2$, or even larger.

The device body area or the area of the apparatus plate corresponding to it is preferably set as appropriate in consideration of factors such as the number of cell plating sections on the apparatus plate and the degree of integration in micromachining described below for the device body. The constituent material of the device body is also not restricted, but preferred examples are inorganic materials such as glass, and organic materials such as plastics. It is particularly preferred to use a transparent material.

A board-shaped device body preferably has an upper board provided with a suspension supply port and a lower board provided with a suspension injection port, both joined in a closely bonded state, with a groove forming the suspension flow channel formed on at least the bonding surfaces of the upper board and the lower board. The cross-sectional shape of the groove may be semicircular or quadrilateral. In this case, the groove essentially forms the suspension flow channel after the upper board and lower board have been joined. When grooves are formed in both the upper board and lower board precisely corresponding to semicircular cross-sections, the result is that a circular cross-sectional suspension flow channel is formed.

However, the board-shaped device body may be a single board so long as it can be worked to form a plurality of suspension flow channels inside it. Such working can be accomplished by a stereolithographic method (three-dimensional stereolithography) using a photocuring resin, although the production efficiency is reduced.

The device body comprises (1) a suspension supply port for external supply of a neuron suspension containing neurons suspended at a fixed density, (2) a plurality of fine suspension flow channels extending in a branched fashion from the suspension supply port inside the device body, and (3) a suspension injection port for injection of the neuron suspension into the cell plating section, opening into the bottom of the device body at the end of each suspension flow channel.

When the neuron seeding device is placed on the apparatus plate of the culturing device for formation of a neuron network or the planar patch-clamp device, the individual suspension injection ports must be located to precisely correspond with the individual cell plating sections. Also, as mentioned above, for precise positioning of the suspension injection port and the cell plating section during placement of the neuron seeding device, it is preferred to display a positioning label (marker) on the device body made of a transparent material, or on the apparatus plate of the culturing device for formation of a neuron network or the planar patch-clamp device.

The suspension supply port of (1) opens out onto the top side of the device body. Even if it opens out onto the side of the device body, however, it is usable so long as the suspension supply port slopes diagonally downward toward the main body interior. Furthermore, assuming that the neuron suspension is to be supplied in a pressurized state into the suspension supply port, when leakage of the neuron suspension from the suspension supply port after the neuron seeding procedure has been completed is not a concern, the suspension supply port may open out in the horizontal direction on the side of the device body.

The suspension supply port may be provided at only one location of the device body, but when a considerably large number of fine suspension flow channels of (2) and suspension injection ports of (3) have been set, it is preferred to provide suspension supply ports at numerous locations of the device body, appropriately dispersed, from the viewpoint of facilitating communication by the flow channel design. When suspension supply ports are provided at numerous locations, supply of neuron suspension to the ports may be accomplished using separate injectors or the like for each, or alternatively a connecting pipe having a single pipe at the base end and branching into multiple pipes at the distal end, may be connected to a single injector or the like at the base end, and the multiple pipes at the distal end each connected to suspension supply ports at the numerous locations.

In either case, the inner diameter of each suspension supply port will usually be as small as from about several hundred μm up to a few mm, for example, and therefore as stated above under "Effect of the Invention", a connecting pipe having a tapered tip end may be inserted into the injection hole of a liquid injecting tool such as an injector or microsyringe, and the tapered section at the tip end may be inserted into the suspension supply port. The "tapered section at the tip end" of the connecting pipe may be, for example, a stainless steel insertion nozzle formed into a conical shape that gradually narrows toward the tip. Even when a "connecting pipe branching into multiple pipes at the distal end" is used to supply the neuron suspension to suspension supply ports at multiple locations, it is possible to mount the insertion nozzle at each of the tip sections of the branched pipes.

The suspension flow channels of (2) above may be, for example, fine flow channels with an inner diameter of about 50 μm to 500 μm. The cross-sectional shapes of the suspension flow channels may be circular, semicircular, quadrilateral or the like. Basically, the suspension flow channels are formed along essentially the planar direction in the device body. The suspension flow channels extend as multiple branches from the suspension supply port, and the form of the branches will sometimes be extensions as multiple branched suspension flow channels directly from the suspension supply port, or a small number such as one, 2 or 3 main line suspension flow channels from the suspension supply port, with branch-line suspension flow channels connected in order to multiple suspension injection ports branching out from these main line suspension flow channels.

Also, the straight line distances from the suspension supply port to the individual suspension injection ports may depend on the positions where the suspension injection ports are set, and do not need to be the same. However, for the reasons explained in regard to the effect of the tenth invention, it is highly preferred for the lengths from the suspension supply port of (1) to the suspension injection ports of (3) in the plurality of suspension flow channels to be set so that they are substantially the same. This condition can be met if, for example, a by-pass section for adjustment of the flow channel length is purposely set in a suspension flow channel that is a specified main line, and/or in a suspension flow channel that is a specified branch line.

In regard to the suspension injection ports of (3), each suspension injection port is set so as to be positioned at an individual cell plating section. The suspension injection ports open out downward into the flat bottom of the device body. Also, as mentioned above, when the device body is set on the apparatus plate of the culturing device for formation of a neuron network or the planar patch-clamp device, the bottom of the device body contacts with the apexes of the plurality of protrusions of the cell plating section. The neuron suspension injected through the suspension injection ports is thus reliably injected inside the cell plating section. For this reason, the opening diameters of the suspension injection ports are preferably about the same as the inner diameter of the cell plating section defined by the plurality of protrusions, or just slightly smaller or slightly larger.

The device body preferably further comprises a second suspension flow channel system for injection of neuron suspension into the regions other than the cell plating section of the apparatus plate of the culturing device for formation of a neuron network or the planar patch-clamp device, for the reasons explained above in regard to the effect of the thirteenth invention.

The second suspension flow channel system may have second suspension supply ports with similar structures as those of (1) above, for example, provided at an appropriate number of locations on the board-shaped device body. In this case, the second suspension supply ports may penetrate to the bottom of the device body without passing through the fine suspension flow channels, or they may communicate with the second suspension injection ports similar to (3) that open into the bottom of the device body after branching into a plurality of second suspension flow channels similar to (2). In the second suspension flow channel system, the plurality of second suspension flow channels do not need to be set to have substantially the same lengths.

EXAMPLES

Examples of the invention will now be described. However, the technical scope of the invention is not limited by these examples.

First Example

Figure 5:
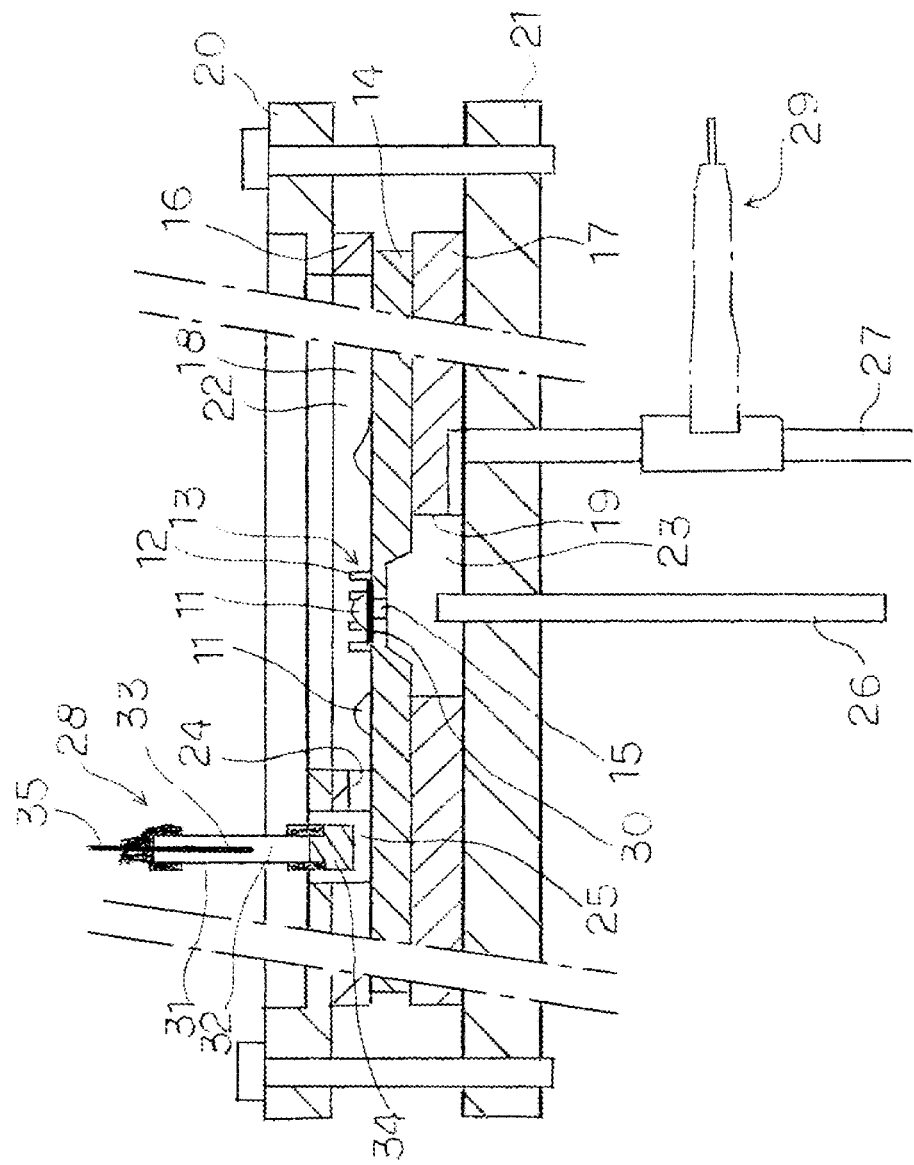
FIG. 5 is a cross-sectional view of the first example.

A device according to the first example is shown in FIG. 5. This device has a culturing device for formation of a neuron network, constructed as a culturing planar patch-clamp device to serve as an ion channel biosensor.

The electrical insulating plate 14 used in this device was a silicon plate. The plate 14 is provided with fine through-holes 15 having diameters of 1 to 3 μm, that allow communication between a first surface side (the top end in the diagram) and a second surface side (the bottom end in the diagram). In FIG. 5, one fine through-hole 15 is provided at the center of the plate 14, but a larger plate may be used and a plurality or many fine through-holes 15 provided, with the following construction applying to each of the fine through-holes 15.

A cell plating section 13 is formed surrounded by a plurality of protrusions 12 on the plate surface above the opening on the first surface side of the fine through-hole 15, with one to several neurons 11 being placed in the cell plating section 13 (only one neuron is shown in the diagram for convenience).

The plate 14 is sandwiched between the first surface side and second surface side by a pair of spacers 16, 17. The constituent material of the spacers 16, 17 is not restricted, but the spacer 16 on the first surface side is preferably an elastic, optically opaque material, and for example, silicon rubber, PDMS (polydimethylsiloxane) or the like may be used. On the other hand, the spacer 17 on the second surface side is preferably an optically transparent material.

At the center section of the spacer 16 there is formed a notch as a large culturing space 18 for construction of a neuron network, and on the plate 14 surface in this culturing space 18 there are formed one, several or many cell plating sections 13 in which a neuron 11 is placed (the diagram shows only a single cell plating section for convenience). Neurons 11 are also seeded at sections other than the cell plating section 13 on the plate 14 surface.

In the spacer 17, a notched section 19 which is circular, for example, is formed at the section corresponding to the fine through-hole 15 of the plate 14, whereby the opening in the second surface side of the fine through-hole 15 opens out into the notched section 19. Thus, the notched section 19 may also be one, several or many, corresponding to the cell plating sections 13 and the fine through-holes 15 (although only one notched section 19 is shown in the diagram for convenience).

In addition, the entirety of the plate 14 and the pair of spacers 16, 17 have a structure that is clamped by a pair of strong plates 20, 21. The material of the plates 20, 21 is not particularly restricted so long as it is a material that can withstand autoclave sterilization at about 120° C. However, the plate 20 on the first surface side is preferably made of an optically opaque material. On the other hand, the plate 21 on the second surface side is preferably made of an optically transparent material.

In the construction described above, a notched section that is circular, for example, is provided at the center section of the plate 20 on the first surface side, at a location corresponding to the culturing space 18 of the spacer 16 on the first surface side, having a size similar to that of the culturing space 18. On the circumference of the notched section there may be formed a recess-like step where the thickness of the plate is reduced, and a covering member (not shown) such as cover glass may be placed on the step as a construction to allow opening and closing of the opening of the notched section in the spacer 16. A main pool 22 is thus constructed on the first surface side.

On the other hand, a liquid pool section 23 is formed on the second surface side by using the plate 21 to plug the opening of the notched section 19 at the spacer 17 on the second surface side. The main pool 22 on the first surface side and the liquid pool section 23 on the second surface side are connected via the fine through-hole 15.

The main pool 22 forms the first region of the liquid pool section on the first surface side. The main pool 22 is connected with a secondary pool 25 forming the second region of the liquid pool section on the first surface side, through a narrow liquid flow channel 24 provided in the spacer 16. The secondary pool 25 is formed by a hole formed through both the spacer 16 and the plate 20. An electrode section 28 on the first surface side, described below, is situated in the secondary pool 25.

A cell culture medium as conducting liquid is introduced into and held in the liquid pool section on the first surface side composed of the main pool 22, liquid flow channel 24 and secondary pool 25. Neurons may be dispersed in the conducting liquid. The conducting liquid used may be a buffering solution comprising 140 mM NaCl, 3 mM KCl, 10 mM 4-(2-hydroxyethyl)-1-piperazineethanesulfonic acid (HEPES), 2.5 mM $CaCl_2$, 1.25 mM $MgCl_2$ and 10 mM glucose at pH 7.4 (with HCl), or cell culture medium such as Dulbecco's modified Eagle's medium (DMEM: Sigma) with addition of 10% (v/v) FBS and 1% (v/v) Glutamax™ (Gibco). The composition of the conducting liquid can be appropriately changed depending on the type of neuron.

Into the liquid pool section 23 on the second surface side there is introduced a buffering solution or cell culture medium, known as a pipette solution, which may be 40 mM CsCl, 80 mM $CsCH_3SO_4$, 1 mM $MgCl_2$, 10 mM HEPES, 2.5 mM MgATP, 0.2 mM $Na_2EGTA$ (pH 7.4). Introduction of the conducting liquid into the liquid pool section 23 is accomplished through a tubular liquid introduction flow channel 26, and discharge is accomplished by a liquid discharge flow channel 27. In this example, PEEK tubes with an outer diameter of 1 mm and an inner diameter of 0.5 mm were used for the liquid introduction flow channel 26 and liquid discharge flow channel 27, but the constituent materials of these liquid flow channels may be other materials instead, so long as the materials can withstand autoclave sterilization at about 120° C.

In the liquid discharge flow channel 27 there is set an electrode section 29 on the second surface side formed in the same manner as the electrode section 28 on the first surface side (shown in outline fashion by a dash-dot line). The construction of the electrode sections 28, 29 will be described below. Normally, the electrode of the electrode section 28 on the first surface side is grounded, and a membrane voltage is applied to the electrode of the electrode section 29 on the second surface side.

When the conducting liquid in which the neurons 11 are dispersed has been introduced into the main pool 22, and the conducting liquid of the liquid pool section 23 is suctioned with an appropriate liquid-suction device connected to a liquid discharge flow channel 27, the conducting liquid of the main pool 22 is also suctioned through the fine through-hole 15. By this procedure, it is possible to effectively place a neuron 11 in the cell plating section 13 shown in FIG. 5 (that is, the location of the opening of the fine through-hole 15).

Furthermore, the suction pressure can form fine pores in the cell membrane of the neuron 11 at the portion contacting with the fine through-hole 15. For formation of such pores in the neuron 11 there may also be mentioned a method of introducing a solution of a cell membrane pore-forming penetrating antibiotic such as nystatin or amphotericin B, from the liquid introduction flow channel 26 into the liquid pool section 23 on the second surface side. When such pores are formed in the cell membrane, the liquid pool section 23 on the second surface side is in a state of electrical conduction with the interior of the neuron.

On the other hand, as means for placing the neuron 11 in the cell plating section 13 (the open location of the fine through-hole 15), an extracellular matrix-forming substance 30 with cell-anchoring force may be adhered to the periphery of the opening on the first surface side of the fine through-hole 15 of the plate 14.

In this construction, when the prescribed ion channel is being expressed on the neuron 11 and a stimulator that opens the ion channel is added to the liquid pool section on the first surface side, the ion channel opens and a channel current corresponding to the applied voltage flows between the electrode section 28 on the first surface side and the electrode section 29 on the second surface side. When a gap is present between the cell membrane of the neuron 11 and the plate 14 during this time, the seal resistance is lowered and leak current is superimposed on the channel current.

The membrane potential has induced voltage by electromagnetic waves present between the space, an interface potential between the electrode metal surface and the buffering solution surrounding it, and a liquid/liquid interface potential, superimposed in addition to the voltage actually applied between the electrodes, and therefore the leak current varies in accordance with the variation in induced noise and interface potential. Thus, noise appears as fluctuation of the baseline with respect to the ion channel current.

The detailed data will not be shown here, but in a pipette patch clamp that can easily provide seal resistance at or above the gigaohm level, the effect of baseline fluctuation noise is small enough to be ignored even with a relatively large fluctuation in membrane potential. However, this fluctuation in membrane potential must be reduced for a culturing planar patch-clamp with relatively low seal resistance (up to 10 MΩ). For this example, a stable electrode was developed having low fluctuation in membrane potential. Such an electrode allows measurement to be carried out with significantly reduced fluctuation in membrane potential and minimal noise current even with low seal resistance.

The structures of electrode sections 28, 29 on the first surface side and second surface side will now be described, without a detailed diagram. The interior of the tubular electrode receptacle 31 composed of Pyrex® glass with an inner diameter of 1 mm is filled with an electrode solution 32 with KCl and AgCl dissolved to saturated concentrations. The KCl concentration was 3.3 M/L and AgCl was added to approximately 1.1 mM/L. For KCl, the saturated concentration is approximately 3.3 M/L at ordinary temperature. For the AgCl/Ag electrode 33 housed in the electrode receptacle 31, AgCl is coated onto the surface of a silver wire. Such an AgCl/Ag electrode 33 can be formed by coating AgCl powder onto the surface of a silver wire, or by dipping a silver wire into a bleaching agent or the like containing sodium hypochlorite. Alternatively, it can be formed by electroplating in a KCl solution.

The tip section of the electrode receptacle 31 is plugged with an inorganic porous material 34 such as porous glass or porous ceramic. The inorganic porous material 34 actually used was Vycor glass (Corning, Inc.). The tip of the inorganic porous material 34 composing a part of the receptacle wall of the electrode receptacle 31 is dipped in a conducting liquid (cell culture solution or buffering solution). The KCl concentration in the conducting liquid is a few millimoles, but since mixing between the electrode solution 32 and the conducting liquid outside the receptacle is small enough to be ignored while the inside and outside of the electrode receptacle 31 are in a state of electrical conduction, due to the effect of the inorganic porous material 34, a large KCl concentration difference is maintained between the inside and outside of the receptacle, thereby maintaining a fixed AgCl/Ag electrode 33 interface potential and liquid/liquid interface potential. The base section of the electrode receptacle 31 is sealed with a sealant, and the electrode pin 35 protrudes from it.

When the channel current is controlled using cells expressing ion channels where the channels open in response to light, placement of the electrode sections 28, 29 on the first surface side and the second surface side causes a liquid pool section on the first surface side to be formed by an optically opaque spacer 16 or plate 20, and therefore light irradiated onto the main pool 22 is not irradiated onto the AgCl/Ag electrodes of the electrode sections 28, 29 on the first surface side and the second surface side. In addition, since a neuron 11 is placed in the main pool 22 and the potassium ion concentration of the conducting liquid on the exterior of the cell is as small as about several mM, it is preferred to minimize the effect of KCl leaking from the electrode section even if it is a trace amount, and for this purpose a secondary pool 25 is formed in addition to the main pool 22 in the liquid pool section on the first surface side, the main pool 22 and secondary pool 25 being connected by a narrow liquid flow channel 24 with a width of no greater than 1 mm.

Second Example

Figure 6:
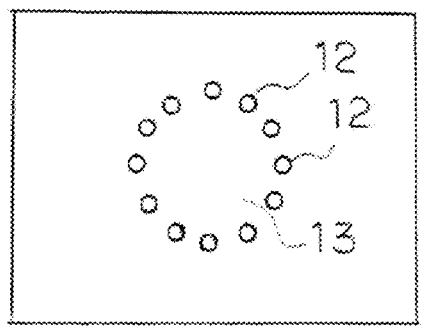
FIG. 6 is an overview of the second example.
Figure 6:
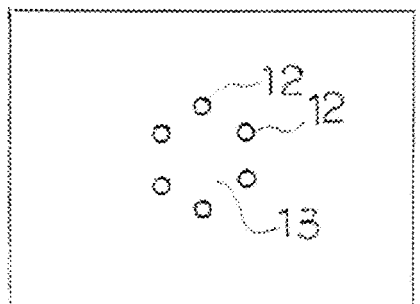
Figure 6:
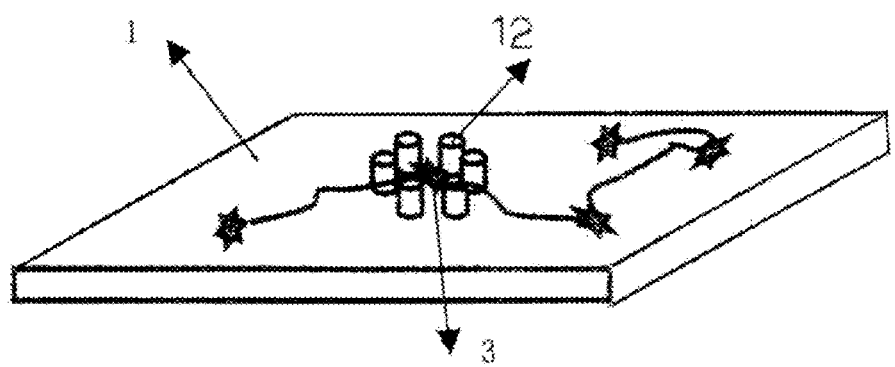

A second example is shown in FIG. 6. The second example and the following third example further demonstrate in detail the essential points of the first example. The part numbers in these examples differ from those of the first example, but the same part names have essentially the same structures.

A negative photoresist SU8 is coated onto the surface of a Si plate 1 to a thickness of 8 to 10 μm using a spinner, and a previously prepared photomask is used for development by a common process, to form a cell plating section 13 composed of a plurality of palisaded protrusions 12, examples of which are shown in FIG. 6(*a*) and FIG. 6(*b*).

The protrusions in this case are square columns with bottoms of 10 μm×10 μm and heights of 8 to 10 μm, the mutual gaps between the protrusions being 8 to 10 μm. The diameters of mouse or rat cerebral cortical or hippocampal neuronal cell bodies are generally about 10 μm when seeded and 15 to 20 μm when plated, and therefore the neuron 3 situated in the cell plating section 2 formed by the plurality of protrusions does not migrate out of the cell plating section 2. However, the cell culture medium migrates into the cell plating section 2 so that culturing of the cell takes place satisfactorily in the cell plating section 2. The shapes of the protrusions may be circular columnar or elliptic cylindrical, and may even be solid spherical.

Placement of the neurons 3 by the cell plating section 13 composed of the plurality of protrusions 12 is useful for formation of a neuron network. As shown conceptually in FIG. 6(*c*), placing a neuron 3 on the inside of the cell plating section 13 results in formation of a network with the neurons 3 on the outside of the cell plating section 13. In such network formation, the neuron 3 undergoes elongation of the axon to bind with adjacent neurons, while neurotransmitters are released from the tip of the axon, while the neurons 3 at the receiving end receive the neurotransmitters and extend their dendrites, forming synaptic junctions.

It is a feature of the invention that the neuron 3 inside the cell plating section 13 and the neurons 3 outside the cell plating section 13 are present on the same flat surface of the plate 1, so that communication between the neurons is accomplished without interference, stable culturing is continued, and a stable network is formed. In the case of this example, the neuron 3 situated inside the cell plating section 2 could be cultured for a month or longer.

It is useful in many respects to form a network by setting the locations of the neurons in this manner. The effect is particularly notable when applying a planar patch-clamp device for culturing, such as shown in FIG. 5.

The inner diameter of the cell plating section 13 can be easily changed as shown in FIG. 6(*a*) and FIG. 6(*b*). The inner diameter may be the inner diameter allowing numerous (comparatively numerous) neurons 3 to be placed for stable culturing of the neuron network for a prolonged period, or an inner diameter allowing one to a small number of neurons 3 to be placed for easy functional analysis of a network, determined based on the optimal number of neurons (cluster size) for the purpose. For example, a cluster of 1 to 4 is satisfactory for relatively hardy rat cerebral cortical neurons, but with relatively fragile iPS cells or neurospheres differentiated and induced from them, clusters comprising more numerous cell bodies are preferred for stable culturing.

Third Example

A third example will now be described based on FIG. 7. In this diagram, the circled section labeled "c" at the bottom right of FIG. 7 (A) is a magnified section of the cross-section near the fine through-hole 4 at the center section of the cell plating section 2. The culturing planar patch-clamp has a construction with a fine through-hole 4 with a diameter of 1 to several μm formed in a plate 1 such as Si, or plastic, ceramic or glass, a neuron 3 being placed over the fine through-hole 4, and a prescribed buffering solution filling both above and below the plate 1, and with an upper electrode 7 and lower electrode 8 installed. The lower electrode 8 is connected to a current amplifier 5.

Fine pores are opened in the cell membrane of the neuron 3 contacting with the fine through-hole 4, forming a whole-cell state with electrical conduction between the neuron 3 and the buffering solution pool below the plate 1. The method of opening fine pores in the neuron 3 is a method of applying negative pressure to the lower liquid pool to breach the cell membrane, as explained for the first example. Another method involves causing a buffering solution dissolving antibiotics such as nystatin and amphotericin to flow into the lower liquid pool, and implanting the antibiotics into the cell membrane to produce a state of electrical conduction between the cell interior and the lower liquid pool.

In this case, coating an extracellular matrix-forming substance 9 onto the surface of the plate 1 surrounding the fine through-hole 4 is effective for prolonging the lives of the neurons 3. While many extracellular matrix-forming substances 9 are known, poly-L-lysine and laminin are among those more well known. For seeding of the neurons 3 into the system, it is particularly effective to utilize a micropipette 6 such as shown in the diagram, since it is necessary to reliably seed a single cell or a plurality of cells inside the cell plating section 2.

Figure 7:
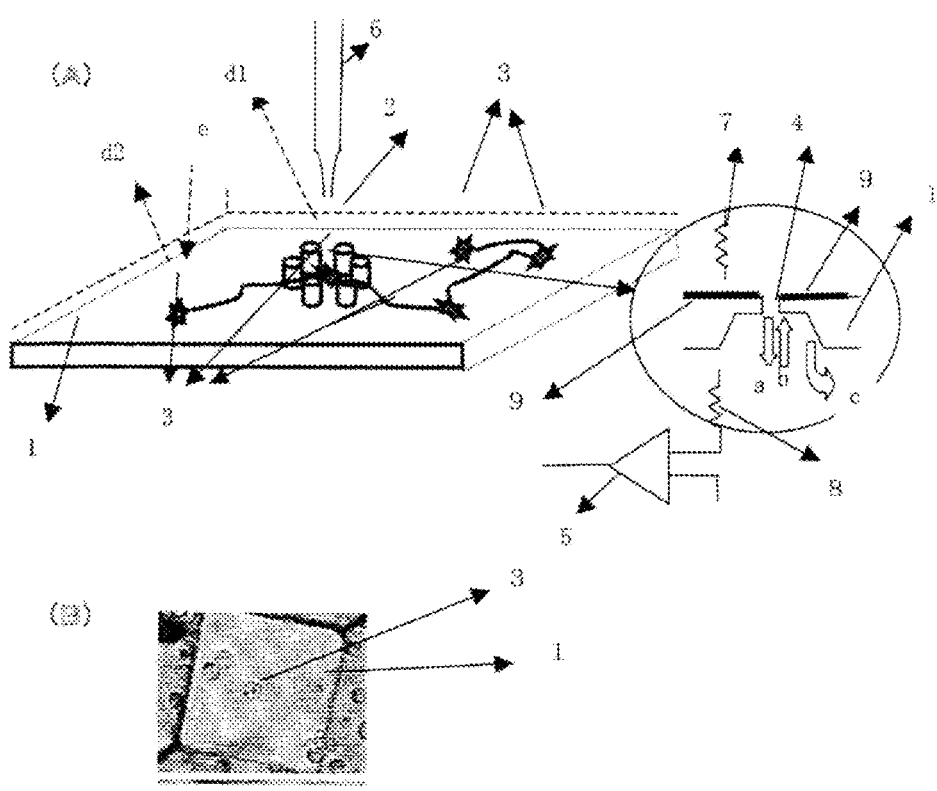
FIG. 7 is an overview of the third example.

Furthermore, in this case, as shown by the circled section labeled "c" in the partial magnified view at the bottom right of FIG. 7 (A), the suspension of a neuron 3 is injected onto the cell plating section 2 at a prescribed rate from the micropipette 6 while a prescribed negative pressure is applied to the lower liquid pool, so that the neuron 3 can be efficiently placed on the fine through-hole 4 as shown in FIG. 7 (B). If the negative pressure is too great, however, the neurons 3 will die, and therefore appropriate pressure must be set for each type of cell. In FIG. 7 (B), in a suction experiment using HEK293 cells, it was confirmed that neurons 3 do not suffer damage if the negative pressure is 2 kPa. It was also confirmed that 80% of the neurons 3 do not suffer damage if the negative pressure is 5 kPa. However, it was confirmed that if the suction pressure begins to be removed immediately after the neurons 3 have been placed on the fine through-holes 4 by suction, the extent of damage is minimal.

In this example, a probe molecule for Ca imaging was introduced into the neurons 3 beforehand. Also, the neurons 3 also expressed photoreceptor ion channels such as channel rhodopsin by gene transfer, allowing stimulation by light such as laser light. In this case, it is important for the excitation wavelength of the channel rhodopsin and the excitation wavelength of the Ca probe molecule to be sufficiently separate so that they do not interfere. The excitation wavelength of the channel rhodopsin utilized in this example was 470 to 480 nm, while the Ca probe used was Oregon Green BAPTA-1 having an excitation wavelength of 494 nm and a luminous wavelength of 523 nm. The operational modes implemented in this third example were the following four types.

(First Operational Mode)

A prescribed membrane potential (normally from −80 to +80 mV) is applied to the neuron 3 on the fine through-hole 4 by an upper electrode 7 and a lower electrode 8, and the ion channel current flowing in the neuron 3 by spontaneous firing is observed in whole-cell mode (arrow symbol "a" in FIG. 7(A)). In this case, synaptic current of $Na^+$, $K^+$, $Cl^-$ and the like is observed with the inflow of Ca ion by spontaneous firing of the surrounding neurons 3 and the reception of neurotransmitters (K. S. Wilcox et al., Synapse 18 (1994) 128-151), and this can yield information regarding the state of the axons and the state of the neurons 3.

(Second Operational Mode)

A prescribed current is injected into the neuron 3 on the fine through-hole 4 by the upper electrode 7 and the lower electrode 8, or voltage is applied (the arrow symbol "b" in FIG. 7 (A)) to stimulate the neuron 3 and generate an action potential. This causes influx of Ca ions into the stimulated neuron 3. Thus, the fluorescence of the Ca probe is observed (the arrow symbol "d1" in FIG. 7 (A)), while the generated action potential is propagated to the surrounding neurons 3, producing luminescence of the Ca probe in the surrounding neurons 3 (the arrow symbol "d2" in FIG. 7 (A)). Observation of this luminescence allows propagation of the signal to be confirmed. That is, information can be obtained regarding the signal propagation properties of the neuron network.

(Third Operational Mode)

Laser light of 470 to 480 nm is focused and irradiated on a single neuron 3 present near the neuron 3 on the fine through-hole 4 (in the cell plating section 2) and expressing channel rhodopsin (the arrow symbol "e" in FIG. 7 (A)), generating an action potential in the single neuron 3. Thus, the action potential signal is propagated to the neuron 3 on the fine through-hole through the network, and the Ca channels are opened inducing influx of Ca ions. As a result, it is possible to observe ion channel current by the upper electrode 7 and the lower electrode 8 that are applying a membrane potential to the neuron 3 on the fine through-hole, previously set to whole-cell mode. According to the third operational mode, the signal propagation properties of the neuron network can be measured on the single cell level and analyzed in detail.

(Fourth Operational Mode)

In the first to third operational modes, the structure shown in FIG. 7(A) which is a combination of the cell plating section 2 and the fine through-hole 4, operates as an element so long as at least one location is present. Also, if a plurality of such structures are formed on the plate 1, it will operate as a high throughput screening device. In contrast, in the fourth operational mode described below, an element is constructed having structures as shown in FIG. 7(A), i.e. one each corresponding to the trigger cell and the follower cell.

A system that is a combination of a fine through-hole 4 and cell plating section 2 as shown in FIG. 7(A) is formed at multiple locations on the plate 1. An action potential is generated in several of the neurons 3 on the fine through-hole 4 (trigger cells) by current injection or voltage application. Also, propagation of the action potential to the other neurons 3 on the fine through-hole 4 (follower cells) can potentially be analyzed by recording the ion channel current of the follower cells in whole-cell mode. In these devices it is very important for the neurons 3 to be placed at specified locations, and it is obvious that the invention is highly useful for formation of a stable neuron network with specified locations.

Furthermore, in the first, third and fourth operational modes, Ca imaging is observed simultaneously not only with the ion channel current at the fine through-hole 4 but also at the top side of the plate 1, thereby allowing functional analysis of the network to be accomplished in a more precise manner, and this is therefore highly effective.

Fourth Example

Figure 8:
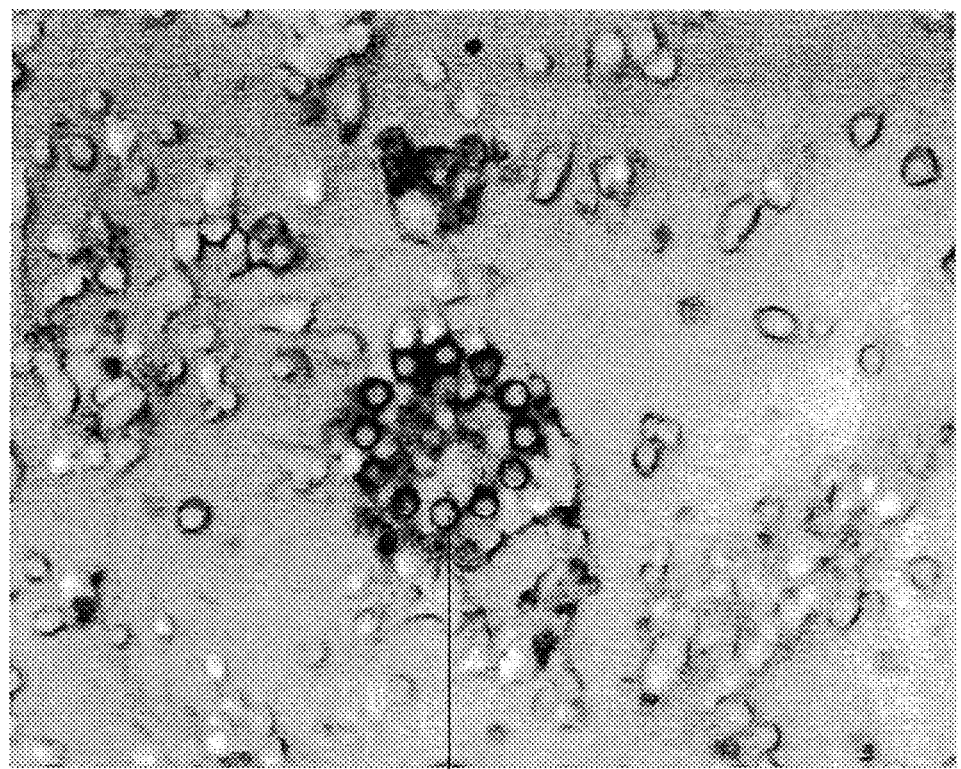
FIG. 8 is an overview of the fourth example.
Figure 8:
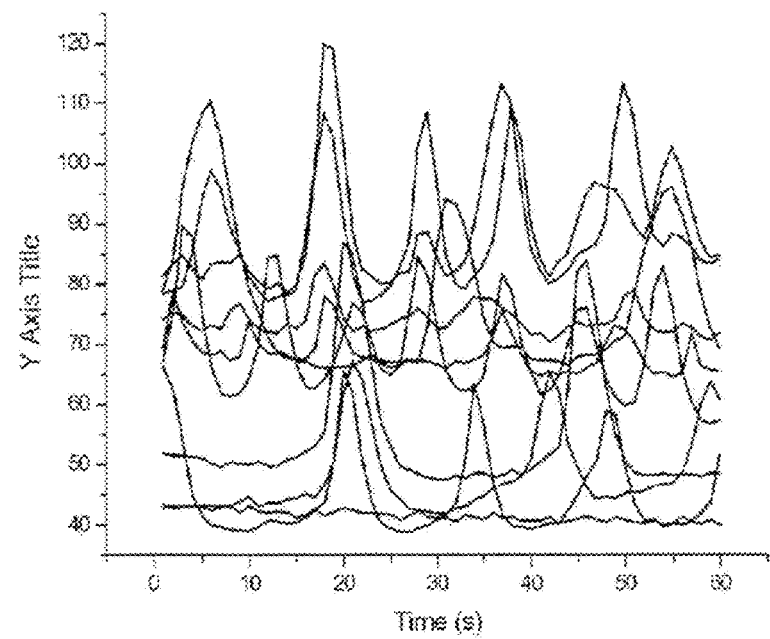

The fourth example is illustrated in FIGS. 8(a) and (b). In FIG. 8(a), which is a flat photograph, a cell plating section 2 comprising circular columns 12 with diameters of about 10 μm and heights of about 8 μm, appearing as a small circle, has been formed on the surface of a Si plate, neurons 3 harvested from 17-day-old rat embryonic cerebral cortex have been seeded, and formation of a neuron network after 14 days of culturing has been confirmed with a fluorescent microscope. After the medium was exchanged with a prescribed buffering solution, Oregon Green BAPTA-1 as a Ca probe was mixed with the buffering solution, and after approximately another 2 hours elapsed, the buffering solution was exchanged with a solution containing no Ca probe and the neurons 3 were observed with a fluorescent microscope.

It can be seen that several neurons 3 are stably situated in the cell plating section 2, and that neurons inside the cell plating section 2 and outside the cell plating section 2 have formed a network. Moreover, FIG. 8(b) shows the results of observing the time-dependent change in fluorescence intensity of the neurons 3 inside the cell plating section 2, where there can be seen repeated active spontaneous firing of the neurons 3 and fluctuation in the Ca concentration inside the neurons 3. In this example, only one the cell plating section 2 group is set, but if numerous such groups are set it is possible to observe the state of signal propagation from a specific cell plating section 2 to another cell plating section 2, and to accurately and stably carry out functional analysis of a network.

Fifth Example

Figure 9:
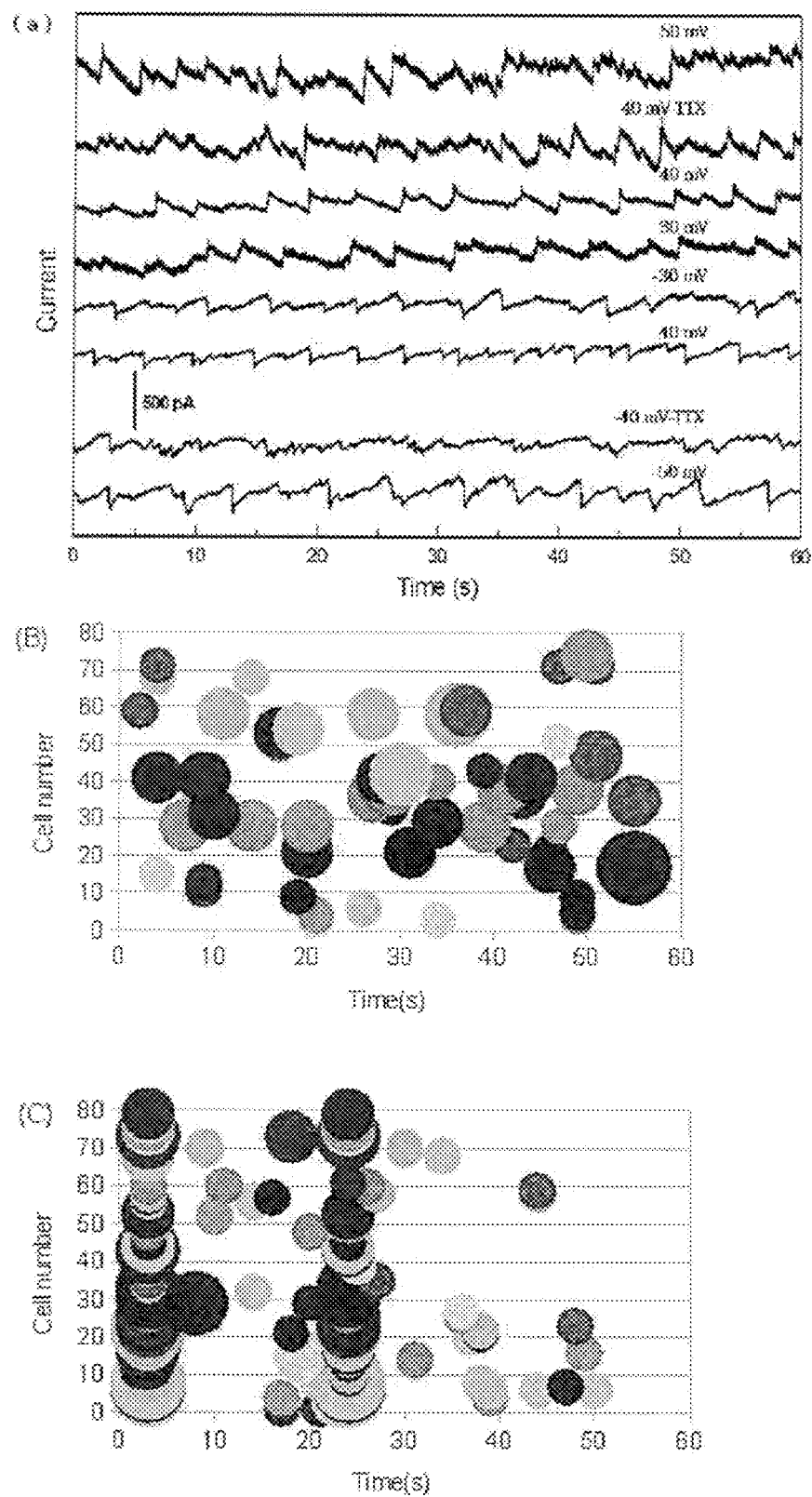
FIG. 9 is an overview of the fifth example.

A fifth example is shown in FIG. 9. A cell plating section composed of a plurality of protrusions surrounding a fine through-hole in a culturing planar patch-clamp element constructed using a Si plate, was formed by the same method as the second example to the fourth example, using a negative photoresist. Neurons harvested from rat embryonic cerebral cortex were seeded by the same method as the fourth example, and after 14 days of culturing, it was confirmed that the neurons in the cell plating section were situated on the fine through-hole and that the neurons had formed a network with the surrounding neurons.

Next, the media on the top side of the plate and the bottom side were each exchanged with prescribed buffering solutions, a 500 μg/ml concentration of nystatin was mixed with the buffering solution on the bottom side, and after standing for approximately 10 minutes, the current flowing into an electrode set on the bottom side of the plate 1 in a whole-cell mode configuration was detected with a current amplifier (Axopatch200B).

The results are shown in FIG. 9(A). FIG. 9(A) shows the membrane potential dependency of the current. Also, 40 mV-TTX is the current observed with a membrane potential of 40 mV, when the Na channel blocker tetrodotoxin (TTX) had been mixed with the buffering solution on the top side. When the membrane potential changes from minus to plus the current waveform orientation switches from down (−) to up (+), and there is exhibited the feature of signal propagation from the spontaneously firing neurons and synaptic current from spontaneous release of neurotransmitters. These waveforms reflect the nature of the network, and the waveform is altered by chemical agents such as antagonists and agonists. Because the area occupied by the cell plating section and fine through-hole is very small it is easy to accomplish multipoint measurement at about 100 points, easily allowing the multipoint measurement necessary for high throughput screening.

FIG. 9(B) and FIG. 9(C) show in summary the results of measuring the time-dependent change in fluorescence intensity by Ca imaging of each of the neurons, from above the plate. The abscissa represents time, and the ordinate represents the numbers assigned to each of the neurons. The sizes of the circles represent the strengths of Ca fluorescence intensity. In FIG. 9(B), the density of the neurons was low at only $2 \times 10^5$ per 35 mm dish, and the luminescence from the neurons was completely random.

In contrast, in FIG. 9(C), the density of the neurons was high at $2 \times 10^6$ per 35 mm dish, thus demonstrating that luminescence by Ca imaging occurs in synchronization. These results mean that it is possible to accomplish more precise measurement and analysis by measuring ion channel current on the bottom side of the plate while simultaneously conducting Ca imaging on the top side.

Sixth Example

Figure 10:
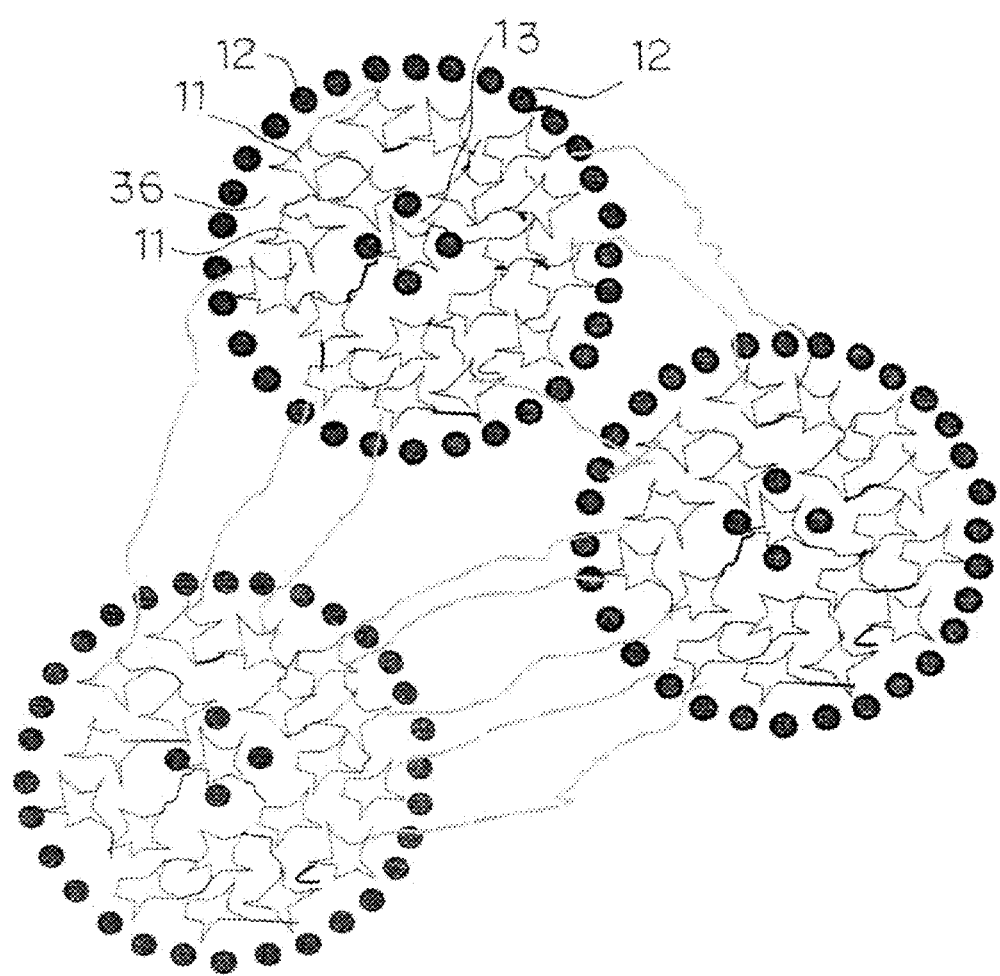
FIG. 10 is an overview of the sixth example.

The sixth example corresponds to a modified example of the cell plating section 13. As shown in FIG. 10, a cell plating section 13 is formed surrounded by a plurality of protrusions 12 in the same manner as the first example, on the plate surface above the opening on the first surface side of the fine through-hole, with the neurons 11 placed in the cell plating section 13. An outer cell plating section 36 is also formed on the outside of the plurality of protrusions 12 forming the cell plating section 13 in a ring shape, and further surrounded by numerous protrusions 12. That is, according to the sixth example, the rings that are formed by the protrusions 12 are in a double ring structure with the cell plating section 13 and the outside cell plating section 36.

Fine through-holes are present in the cell plating section 13 which is the region surrounded by the inner ring, and in this region there are plated 1 to several neurons 11, the neurons 11 being definitely situated on the fine through-hole. Numerous neurons 11 are simultaneously seeded in the outer cell plating section 36, which is the region between the inner ring and the outer ring. Thus, a neuron network is formed not only between the neurons 11 inside the cell plating sections 13 but also between the neurons 11 of the cell plating sections 13 and the neurons 11 of the outer cell plating sections 36.

Such a structure comprising cell plating sections 13 and outer cell plating sections 36 is advantageous in that neurons that are unstable as single cells and cannot be stably cultured without aggregation of a large number of cells, such as iPS cells for example, can be reliably plated as single neurons each on a fine through-hole, while being cultured for prolonged periods in a stable manner.

A seventh example will now be briefly described as an example of a method of seeding neurons 11 separately in a cell plating section 13 and an outer cell plating section 36 according to the sixth example.

Seventh Example

The seventh example corresponds to a neuron seeding device according to the invention. The device body of the neuron seeding device is a device for seeding of neurons in multiple cell plating sections surrounded by a plurality of protrusions on an apparatus plate, set on the apparatus plate of the culturing device for formation of a neuron network or the planar patch-clamp device according to the example described above.

Figure 11:
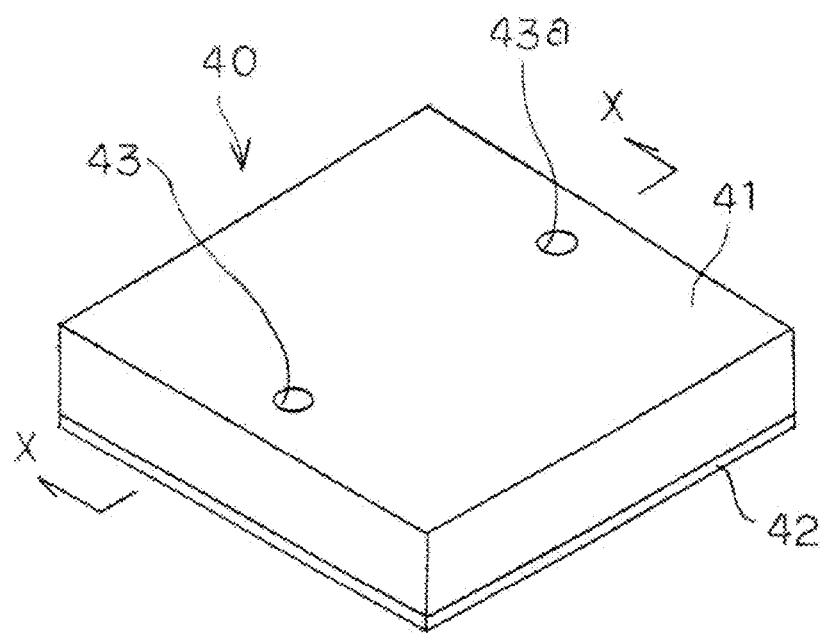
FIG. 11 is an overview of a neuron seeding device main body according to the seventh example.
Figure 11:
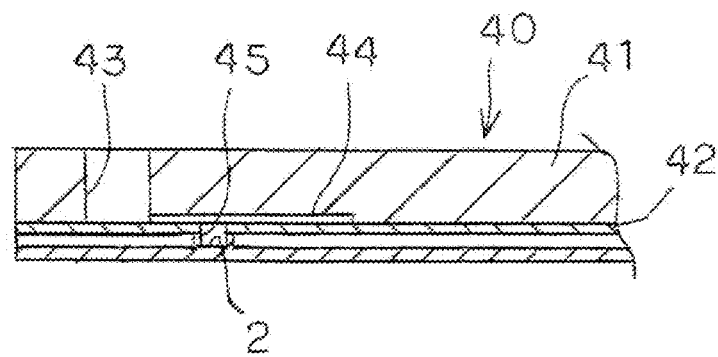

As shown by the perspective view in FIG. 11(a), the device body 40 of the neuron seeding device according to this example is a flat board having a thickness of about 4 to 6 mm and a square planar shape of about 2×2 cm, and it comprises an upper board 41 and a lower board 42. The upper board 41 and lower board 42 are each composed of a transparent plastic such as PDMS (polydimethylsiloxane), PMMA (polymethyl methacrylate) or the like or silicon rubber, that has been surface-cleaned by plasma treatment, for example, and they are heat-bonded together in a closely joined state to form a two-layer structure.

At one side of the center section on the top side of the upper board 41 there is opened a suspension supply port 43 forming a first suspension flow channel system, for external supply of a neuron suspension comprising neurons suspended at a fixed density. Also, at the other side of the center section on the top side there is opened a second suspension supply port 43a forming a second suspension flow channel system. The first suspension flow channel system will be explained first. The second suspension flow channel system will be explained below.

(First Suspension Flow Channel System)

The first suspension flow channel system comprises a suspension supply port, a suspension flow channel and a suspension injection port according to the ninth invention to twelfth invention.

First, a cross-sectional view (partially simplified) along line X-X in FIG. 11(a) is shown in FIG. 11(b), and as shown in FIG. 11(b), fine grooves with inner diameters and depths of both about 50 to 500 μm extend in a branched fashion from the suspension supply port 43 on the bottom side of the upper board 41 (the bonding surface with the lower board 42). Thus, when the upper board 41 and the lower board 42 are joined in a closely bonded state, a plurality of fine suspension flow channels 44 for flow of the neuron suspension are formed by these grooves and the top side of the lower board 42.

FIG. 12(a) shows a lower view (bottom side view) of the upper board 41. While FIG. 11(b) shows only a single suspension flow channel 44, in actuality a plurality of suspension flow channels 44 extend in a branched fashion from the suspension supply port 43 shown at the lower end of the drawing, as seen in FIG. 12(a). By providing extra by-pass routes at appropriate locations in these suspension flow channels 44, the flow channel lengths can be adjusted to be nearly equivalent.

In FIG. 12(a), the suspension flow channels 44 are represented simply by dark solid lines for convenience. The second suspension flow channel 44a, shown here and described below, is also represented simply by a dark solid line.

FIG. 12(b) conceptually shows a top view (plan view) of the plate 1 of a culturing device for formation of a neuron network or a planar patch-clamp device, illustrating five designated plating areas each with a plurality of cell plating sections 2 surrounded by a plurality of protrusions on the top side of the plate 1 (indicated by single dots for simplicity) set in a collective manner. FIG. 12(b) also shows second suspension injection ports 45a, which are described below, although these are in actuality formed by the lower board 42 and not formed on the plate 1, but merely shown in order to highlight the positional relationship with the aforementioned five designated plating areas.

As further explanation based on FIG. 12(a) with the relationship shown in FIG. 12(b), assuming the state where the device body 40 of the neuron seeding device is set on the plate 1, the plurality of suspension flow channels 44 extending in a branched fashion from the suspension supply port 43 each arrive at a point right above the five designated plating areas in which the plurality of cell plating sections 2 on the plate 1 are set in a collective manner, and at those locations they form five injection hole sections 46 communicating with the plurality of suspension injection ports 45 formed on the lower board 42.

Figure 12:
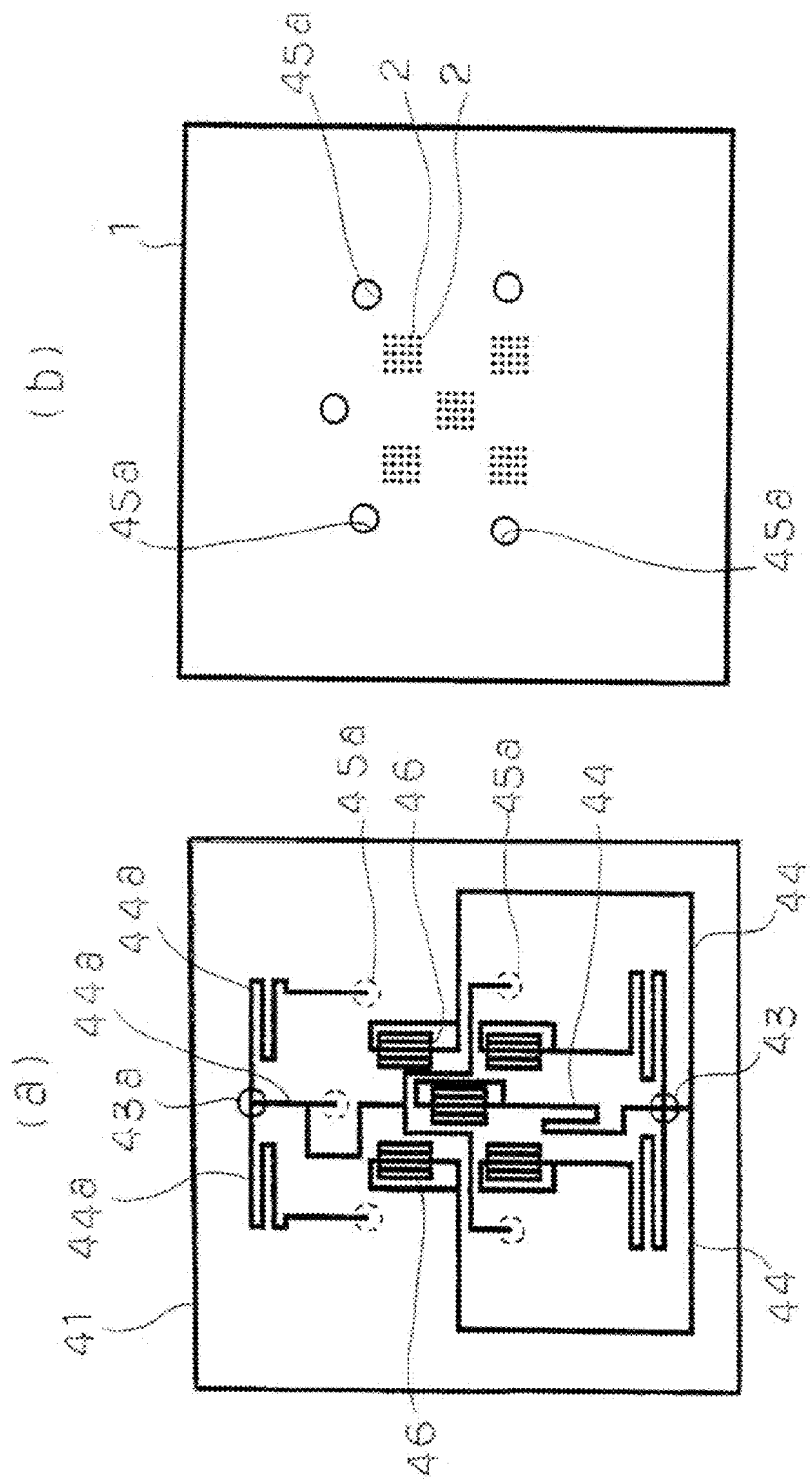
FIG. 12 is an overview of first and second suspension flow channel systems according to the seventh example.
Figure 13:
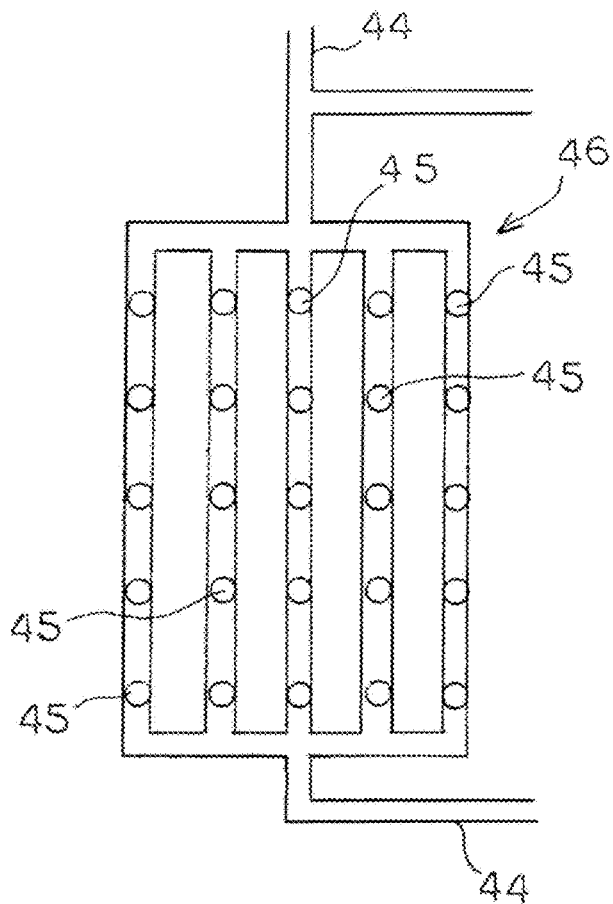
FIG. 13 shows the details of the essential portion of the first suspension flow channel system according to the seventh example.

FIG. 13 shows a magnified view of the injection hole sections 46. At each of the injection hole sections 46, the suspension flow channel 44 branches into 5 longitudinal flow channels, and the five branched flow channels are each connected to one of a plurality of suspension injection ports 45 provided in the lower board 42. That is, as shown in FIG. 12(b), five rows of cell plating sections 2 are formed in the longitudinal direction in the five designated plating areas on the plate 1, with five cell plating sections 2 included in each row, and five rows of flow channels are situated running in the longitudinal orientation of the suspension flow channels 44, completely corresponding to all of the cell plating sections 2, while suspension injection ports 45 are also formed in the lower board 42, completely corresponding to all of the cell plating sections 2.

The inner diameters of the suspension injection ports 45 are essentially the same as or slightly larger than the sizes of the interior regions of the cell plating sections 2, but smaller than the outer shapes of the cell plating sections 2 including the protrusions 12. Thus, the construction is such that the protrusions 12 do not enter into the suspension injection ports 45.

Consequently, when the neuron suspension is supplied in a pressurized state, for example, to the suspension supply ports 43 composing the first suspension flow channel system, the neuron suspension is injected into all of the total of 250 cell plating sections 2 provided in the five designated plating areas on the plate 1 through the suspension flow channels 44 and the suspension injection ports 45, in a very short period of time and in essentially equal amounts to all. As a result, neurons are seeded in the cell plating sections 2, according to the preferred mode described above under "Effect of the Invention".

(Second Suspension Flow Channel System)

The second suspension flow channel system is a suspension flow channel system for injection of a neuron suspension into the regions other than the cell plating sections of the apparatus plate, according to the thirteenth invention, comprising the second suspension supply port 43a shown in FIG. 11(a), a plurality of second suspension flow channels 44a extending in a branched fashion from the second suspension supply port 43a as shown in FIG. 12(a), and second suspension injection ports 45a formed on the lower board 42 at each of the ends of the second suspension flow channels 44a. Each of the second suspension injection ports 45a are shown as broken lines in FIG. 12(a), and as solid lines in FIG. 12(b).

The structural relationship between the second suspension supply ports 43a, second suspension flow channels 44a and second suspension injection ports 45a, is the same as for the suspension supply port 43, suspension flow channel 44 and suspension injection port 45 shown in FIG. 11(b), for the first suspension flow channel system. In the second suspension flow channel system, however, the flow channel lengths of the plurality of second suspension flow channels 44a may be different, or the second suspension injection ports 45a may open into regions other than the cell plating sections on the plate 1, as shown in FIG. 12(*b*).

Therefore, when the neuron suspension has been supplied in a pressurized state, for example, into the second suspension supply ports 43*a* forming the second suspension flow channel system, neurons are seeded into regions other than the cell plating sections on the plate 1, through the second suspension flow channels 44*a* and the second suspension injection ports 45*a*.

When cell plating sections 13 and outer cell plating sections 36 are formed as according to the sixth example, third suspension flow channels (not shown) for seeding of neurons into the outer cell plating sections 36 may also be formed in the device body 40 in addition to the suspension flow channels 44 and second suspension flow channels 44*a*, into seed neurons in the outer cell plating sections 36 in the device body 40. Alternatively, neurons may be seeded in the outer cell plating sections 36 utilizing the suspension flow channels 44 after the location of the device body 40 on the plate 1 has been slightly shifted.

Eighth Example

As explained above, the first suspension flow channel system formed in the device body 40 of the neuron seeding device is utilized to inject a prescribed concentration of neuron suspension into each of the cell plating sections 2. Also, since the mutual gaps between the plurality of protrusions 12 of the cell plating sections 2 are smaller than the dimensions of the neuronal cell bodies during seeding, with sufficient room allowing easy flow of the medium solution of the neuron suspension (for example, the neuron culture solution), introduction of the neuron suspension from above the cell plating sections 2, with flow of the medium solution, causes the neurons to pool inside the cell plating sections 2 and be seeded therein.

It is thereby possible to seed cells without damage in the multiple cell plating sections 2 in a short period of time, and in an essentially simultaneous manner. As a result, it is possible to stably and easily form a neuron network comprising multiple cell plating sections (multiple channel current measuring points of the planar patch-clamp device).

When the gaps between the protrusions 12 are thus utilized for seeding, it is important to more specifically examine the relationship between the dimensions of the gaps and the cell bodies. Specifically, neuronal cell bodies generally differ in their sizes during seeding and during culturing. Also, the cell body shapes are not perfectly round but rather elongated ellipsoid.

Thus, it is necessary for the mutual gaps between protrusions 12 to be smaller than the smaller value of the minimum dimension of the cell body during seeding (the dimension in the short axis direction) and the minimum dimension of the cell body during culturing, but it is also necessary for them to be formed as large as possible so as to allow the medium solution of the neuron suspension to easily flow out and so that the neuronal axons or dendrites can easily move into and out of the cell plating sections 2.

Figure 14:
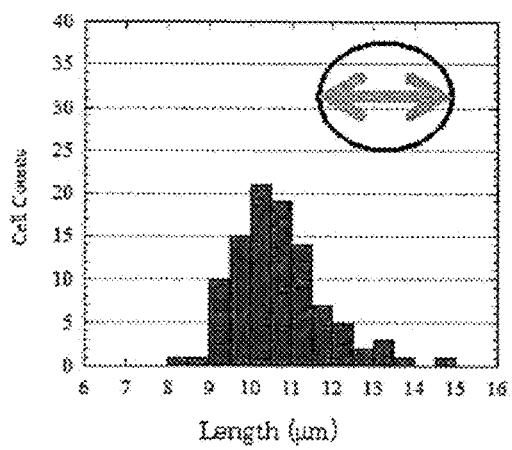
FIG. 14 shows the sizes during seeding of rat hippocampal neurons.
Figure 14:
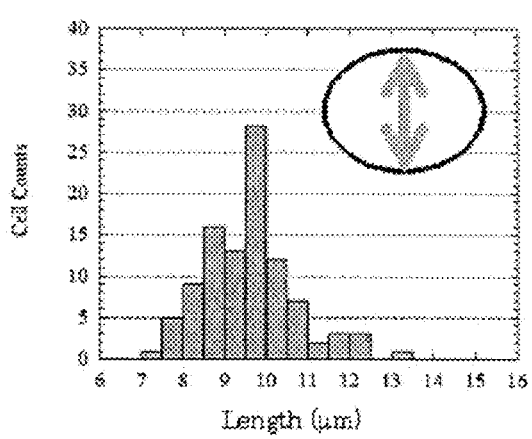

As an example, the results for an experiment with rat hippocampal neurons will now be described with reference to FIG. 14 and FIG. 15. In FIG. 14, the distribution of the maximum dimension (the dimension in the long axis direction) during seeding of numerous rat hippocampal neurons is shown in the graph at the left, and the distribution of the minimum dimension (the dimension in the short axis direction) is shown in the graph at the right). As shown in FIG. 14, the minimum dimension of the cell bodies during seeding was approximately 7.5 μm.

Figure 15:
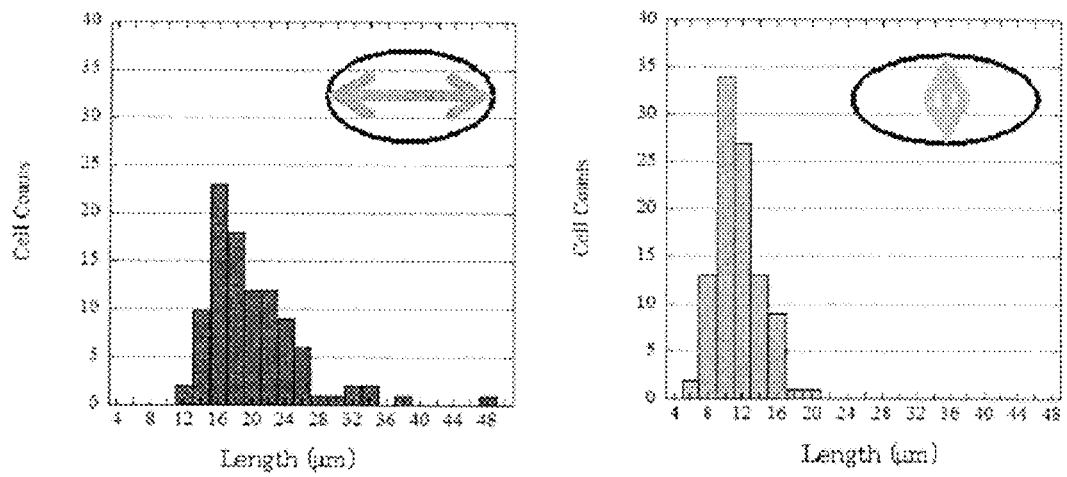
FIG. 15 shows the sizes during culturing of rat hippocampal neurons.

In FIG. 15, the distribution of the maximum dimension (the dimension in the long axis direction) during culturing of the same cell bodies is shown in the graph at the left, and the distribution of the minimum dimension (the dimension in the short axis direction) is shown in the graph at the right). As shown in FIG. 15, the cell bodies were long and narrow during culturing, with the minimum dimensions of the cell bodies being approximately 8 μm.

Figure 16:
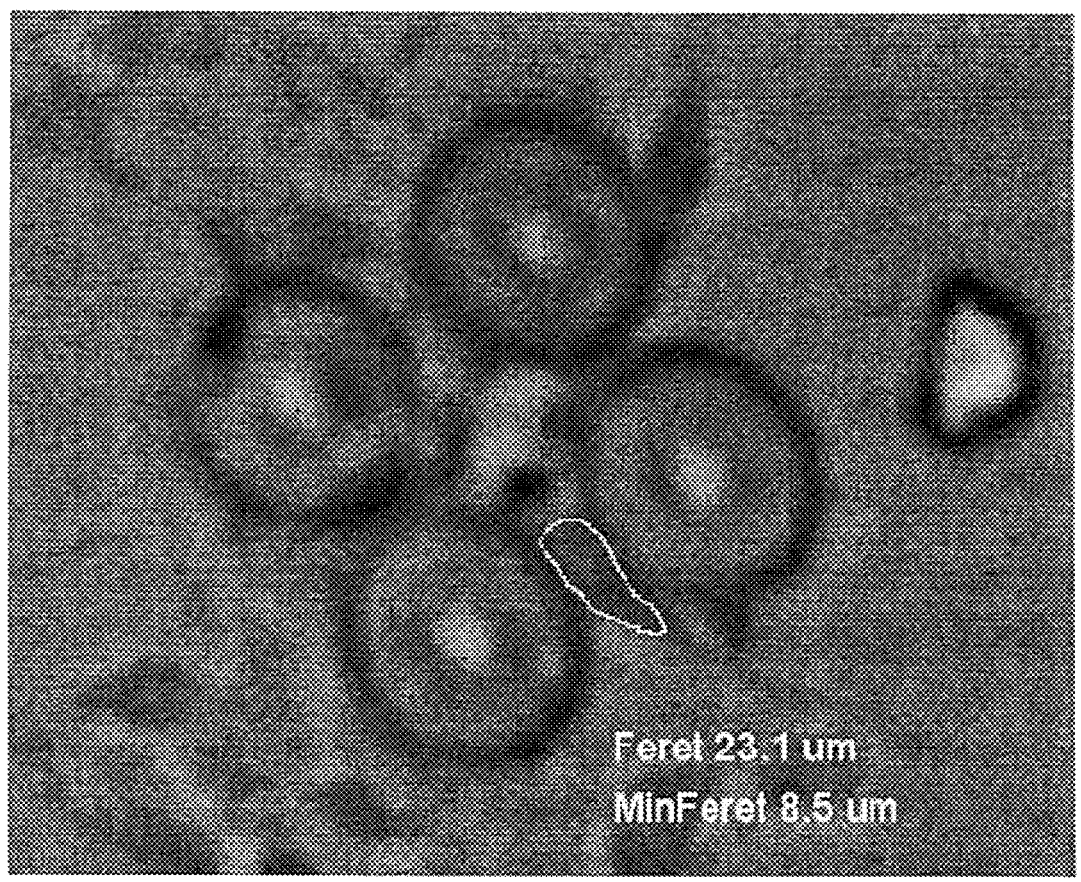
FIG. 16 is an optical microscope photograph showing a separate experiment carried out with rat hippocampal neurons.

A different experiment with rat hippocampal neurons will now also be described with reference to FIG. 16. FIG. 16 is an optical microscope photograph of the state of neurons on the 4th day of culturing, the four large circles in the photograph being four groups of protrusions 12 forming cell plating sections 2, and the outlines indicated by white solid lines representing neurons. As seen in FIG. 16, a neuron is attempting to infiltrate the cell plating section 2 through a gap between the protrusions 12, from the outside. This neuron in fact did not infiltrate but regressed after some elapse of time. The gaps between the protrusions 12 were 11 μm, and the dimensions of the neuronal cell bodies in the short axis direction were 8.5 μm. In the case shown in FIG. 16, therefore, this shows that it is safer for the gaps between the protrusions 12 to be somewhat smaller.

Ninth Example

The ninth example corresponds to a method of preparing a rat neuron suspension to be used for seeding. The suspension was prepared in the following manner. Specifically, cerebral cortexes or hippocampi were harvested from 17- to 18-day-old Wistar Rat fetal brains and the tissue was dispersed with enzyme treatment (37° C., 20 minutes) using a 0.25% Trypsin solution. Next, a cell suspension was prepared at $1.0 \times 10^7$ cells/ml using serum-containing medium with Minimum Essential Medium (MEM) as the basal medium. The cell suspension was introduced and seeded in the cell plating sections using a microflow device or microinjector.

Tenth Example

The tenth example corresponds to preparation of iPS cells to be seeded. Specifically, the human induced pluripotent stem cell (iPS cell) strain 201B7 was obtained from CELL BANK by the independent administrative institution RIKEN (Japan), and STO cell-derived cells (SNL), rendered proliferation impotent by inactivation with mitomycin C, were cultured as feeder cells. Feeder cells are other cells that play a role in aiding in auto-replication of iPS cells.

The culture solution used was mammalian cell-culturing medium (DMEM/F12 medium) containing KSR as serum replacement, L-glutamine, non-essential amino acids and 2-mercaptoethanol, and it was added immediately before using recombinant human basic fibroblast growth factor (bFGF). Seeding was in a 6 cm dish coated appropriately for feeder cells, with a feeder cell concentration of $3 \times 10^4$ cells/cm$^2$, and the iPS cells were seeded on the feeder cells after one day. Satisfactory iPS cells have distinct colony outlines and high inner cell densities. Subcultures of iPS cells are usually at a frequency of once every 3 to 4 days. After subculturing of 3 to 4 generations, in order to induce differentiation to motor neurons, the cells were transferred from culturing on the feeder to a 6 cm dish surface-coated with gelatin or Matrigel, for feederless culturing.

After subculturing for 3 to 4 generations by feederless culturing, differentiation to motor neurons began to be induced. The feederless cultured iPS cells were induced to differentiate to neural stem cells by suspension culture in the presence of a growth factor. The differentiation-inducing medium was DMEM/F12 medium containing added glucose, glutamine, insulin, transferrin, progesterone, putrescine and selenium chloride. The suspension culture step for inducing differentiation was suspension culturing for 2 days at a density of $5 \times 10^4$ cells/ml. The medium was then exchanged with differentiation-inducing medium containing added retinoic acid ($10^{-8}$ M), and suspension culturing was carried out for 4 days. It was again further exchanged with differentiation-inducing medium containing added FGF2 (20 ng/ml) and SHH-N (30 nM), and culturing was carried out for 7 days. As a result of this procedure, the cell forms developed into neural stem cells.

The neural stem cells were dispersed and adhesion culturing was carried out on a culturing dish coated with poly-L-lysine, and differentiation to mature motor neurons occurred by 5 weeks after the start of adhesion culturing. When the neuron network was to be formed on a sensor plate, the plate surface was coated with poly-L-lysine and the dispersed neural stem cells were seeded on it and adhesion cultured for 5 weeks, after which a network containing motor neurons formed. For forming the neuron network on a plate, the plate surface was coated with poly-L-lysine and the dispersed neural stem cells were seeded on it and adhesion cultured for 5 weeks, upon which a network containing motor neurons formed.

INDUSTRIAL APPLICABILITY

According to the invention there is provided a culturing device for formation of a neuron network, allowing a satisfactory neuron network to be constructed with neurons in a live state in cell culture medium while restricting their movement, as well as a means of utilizing the same.

EXPLANATION OF SYMBOLS

1 Plate
2 Cell plating section
3 Neuron
4 Fine through-hole
5 Current amplifier
6 Micropipette
7 Upper electrode
8 Lower electrode
9 Extracellular matrix-forming substance
11 Neuron
12 Protrusion
13 Cell plating section
14 Plate
15 Fine through-hole
16 Spacer
17 Spacer
18 Culturing space
19 Notched section
20 Plate
21 Plate
22 Main pool
23 Liquid pool section
24 Liquid flow channel
25 Secondary pool
26 Liquid introduction flow channel
27 Liquid discharge flow channel
28 Electrode section
29 Electrode section
30 Extracellular matrix-forming substance
31 Electrode receptacle
32 Electrode solution
33 AgCl/Ag Electrode
34 Inorganic porous material
35 Electrode pin
36 Outer cell plating section
40 Device body
41 Upper board
42 Lower board
43 Suspension supply port
43a Second suspension supply port
44 Suspension flow channel
44a Second suspension flow channel
45 Suspension injection port
45a Second suspension injection port
46 Injection hole section

What is claimed is:

1. A planar patch clamp device for analyzing a neuron network, comprising:
    an electrical insulating plate having a first surface, on which a neuron network is formed, a second surface, which is the opposite side, and a through-hole having a diameter which allows passing through both sides of the plate surface, but does not allow the passage of a cell body;
    a first liquid pool section formed on the first surface, which enables holding a conductive solution;
    a second liquid pool section formed on the second surface, which enables holding a pipet solution, and is communicated with the first liquid pool through the through-hole;
    a first surface side-electrode disposed to be electrically conductive to the conductive solution; and
    a second surface side-electrode disposed to be electrically conductive to the pipet solution;
    wherein a cell plating section surrounded by a plurality of protrusions is formed on the first surface so that the protrusions restrict the movement of cells, but allow the formation of a neuron network, the through-hole is arranged in the cell plating section, and the peripheries of the through-hole are coated with an extracellular matrix-forming substance, and
    wherein each of the electrodes on the first surface side and second surface side comprise:
    (a) an electrode receptacle for holding each of the electrodes, wherein at least a portion of the receptacle wall that is in contact with the conductive solution or the pipet solution, when the conductive solution or the pipet solution is introduced into the liquid pool sections, is composed of an inorganic porous material;
    (b) each of the electrodes having a precious metal chloride (NmCl) layer formed on a surface layer section of the precious metal (Nm), and housed in the electrode receptacle; and
    (c) an electrode solution filled into the electrode receptacle, wherein the precious metal chloride (NmCl) and an alkali metal chloride are dissolved at saturated concentration; and
    wherein when cells are plated on the cell plating section, both of the first and second surface-side electrodes are not in contact with a cell body.

2. The planar patch clamp device for analyzing a neuron network according to claim 1, wherein the diameter of the cell plating section defined by the plurality of protrusions is a size that enables accommodating one to several cell bodies.

3. The planar patch clamp device for analyzing a neuron network according to claim 1, wherein the plurality of cell plating sections defined by the plurality of protrusions are arranged on the plate.

4. The planar patch clamp device for analyzing a neuron network according to claim 1, one to several cell bodies are placed in the cell placing section, and another cell body is placed outside of the cell placing section.

5. The planar patch clamp device for analyzing a neuron network according to claim 1, characterized in that the device is used for measurement and analysis of neuronal ion channel current or for imaging analysis.

6. The planar patch clamp device for analyzing a neuron network according to claim 1 further comprising:
- a photodetector for detecting light emitted by neurons; and
- an irradiating device that irradiates light onto the neurons or plate surface.

* * * * *